(12) United States Patent
Gray et al.

(10) Patent No.: US 9,285,325 B2
(45) Date of Patent: *Mar. 15, 2016

(54) PERSONNEL SCREENING SYSTEM

(71) Applicant: Rapiscan Systems, Inc., Torrance, CA (US)

(72) Inventors: Stephen Gray, Salem, OR (US); Ronald Hughes, Garden Grove, CA (US); Jerel Smith, Boulder Creek, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/104,508

(22) Filed: Dec. 12, 2013

(65) Prior Publication Data

US 2016/0041298 A1    Feb. 11, 2016

Related U.S. Application Data

(63) Continuation of application No. 13/047,726, filed on Mar. 14, 2011, now Pat. No. 8,638,904, and a continuation-in-part of application No. 12/887,510, filed on Sep. 22, 2010, now abandoned, which is a (Continued)

(51) Int. Cl.
*G01N 23/04* (2006.01)
*G01V 5/00* (2006.01)

(52) U.S. Cl.
CPC .............. *G01N 23/04* (2013.01); *G01V 5/0008* (2013.01); *G01V 5/0025* (2013.01)

(58) Field of Classification Search
CPC .... G01N 23/04; G01V 5/0008; G01V 5/0025

USPC .................................. 378/57, 62, 86–88, 160
See application file for complete search history.

(56) References Cited

U.S. PATENT DOCUMENTS 3,678,278 A   7/1972   Peil
3,780,291 A   12/1973  Stein (Continued)

FOREIGN PATENT DOCUMENTS

CN   1715895     1/2006
CN   101071109   5/2010

(Continued)

OTHER PUBLICATIONS

Office Action dated Feb. 20, 2015 for U.S. Appl. No. 14/047,604.

(Continued)

*Primary Examiner* — Courtney Thomas
(74) *Attorney, Agent, or Firm* — Novel IP

(57) ABSTRACT

Further, the present specification is directed towards personnel screening systems comprising modular components, including detector and source units, where a dual axis scanning beam is employed. In one configuration, the subject under inspection remains stationary and is positioned between two scanning modules. The X-ray source assembly is designed to minimize the overall system footprint while still yielding the requisite field of view, low radiation exposure level, and required resolution. The modular components allow for a compact, light and yet sufficiently rugged overall structure that can be disassembled for ease of transportation and is also simple to reassemble at a required site for inspection.

23 Claims, 26 Drawing Sheets

Related U.S. Application Data continuation of application No. 12/344,162, filed on Dec. 24, 2008, now Pat. No. 7,826,589, said application No. 13/047,726 is a continuation-in-part of application No. 12/849,987, filed on Aug. 4, 2010, now Pat. No. 8,135,112, which is a continuation of application No. 12/024,320, filed on Feb. 1, 2008, now Pat. No. 7,796,733.

(60) Provisional application No. 61/423,586, filed on Dec. 15, 2010, provisional application No. 61/423,585, filed on Dec. 15, 2010, provisional application No. 61/423,582, filed on Dec. 15, 2010, provisional application No. 61/016,590, filed on Dec. 25, 2007, provisional application No. 60/887,798, filed on Feb. 1, 2007, provisional application No. 61/313,772, filed on Mar. 14, 2010.

(56) References Cited

U.S. PATENT DOCUMENTS

| | | |
|---|---|---|
| 3,790,799 A | 2/1974 | Stein |
| 3,843,881 A | 10/1974 | Barton |
| 3,884,816 A | 5/1975 | Takahashi |
| RE28,544 E | 9/1975 | Stein |
| 3,919,467 A | 11/1975 | Peugeot |
| 3,924,064 A | 12/1975 | Nomura |
| 3,961,186 A | 6/1976 | Leunbach |
| 3,971,948 A | 7/1976 | Pfeiler |
| 3,990,175 A | 11/1976 | Conway |
| 4,008,400 A | 2/1977 | Brunnett |
| 4,020,346 A | 4/1977 | Dennis |
| 4,031,545 A | 6/1977 | Stein |
| 4,047,035 A | 9/1977 | Dennhoven |
| 4,064,440 A | 12/1977 | Roder |
| 4,070,576 A | 1/1978 | Cobb |
| 4,107,532 A | 8/1978 | Macovski |
| 4,112,301 A | 9/1978 | Annis |
| 4,139,771 A | 2/1979 | Dennhoven |
| 4,160,165 A | 7/1979 | McCombs |
| 4,179,100 A | 12/1979 | Sashin |
| 4,196,352 A | 4/1980 | Berninger |
| 4,200,800 A | 4/1980 | Swift |
| 4,228,353 A | 10/1980 | Johnson |
| 4,228,357 A | 10/1980 | Annis |
| 4,242,583 A | 12/1980 | Annis |
| 4,242,588 A | 12/1980 | Huang |
| 4,260,898 A | 4/1981 | Annis |
| 4,298,800 A | 11/1981 | Goldman |
| 4,303,830 A | 12/1981 | Heinzelmann |
| 4,342,914 A | 8/1982 | Bjorkholm |
| 4,349,739 A | 9/1982 | Annis |
| 4,366,382 A | 12/1982 | Kotowski |
| 4,366,576 A | 12/1982 | Annis |
| 4,380,817 A | 4/1983 | Harding |
| 4,389,729 A | 6/1983 | Stein |
| 4,414,682 A | 11/1983 | Annis |
| 4,422,177 A | 12/1983 | Mastronardi |
| 4,426,721 A | 1/1984 | Wang |
| 4,454,605 A | 6/1984 | DeLucia |
| 4,472,822 A | 9/1984 | Swift |
| 4,503,332 A | 3/1985 | Annis |
| 4,514,691 A | 4/1985 | De |
| 4,525,854 A | 6/1985 | Molbert |
| 4,535,245 A | 8/1985 | Zonneveld |
| 4,549,307 A | 10/1985 | Macovski |
| 4,578,806 A | 3/1986 | Grass |
| 4,586,441 A | 5/1986 | Zekich |
| 4,598,415 A | 7/1986 | Luccio |
| 4,672,837 A | 6/1987 | Cottrell |
| 4,692,937 A | 9/1987 | Sashin |
| 4,711,994 A | 12/1987 | Greenberg |
| 4,736,401 A | 4/1988 | Donges |
| 4,745,631 A | 5/1988 | Paolini |
| 4,756,015 A | 7/1988 | Doenges |
| 4,759,047 A | 7/1988 | Donges |
| 4,768,214 A | 8/1988 | Bjorkholm |
| 4,783,794 A | 11/1988 | Dietrich |
| 4,799,247 A | 1/1989 | Annis |
| 4,807,637 A | 2/1989 | Bjorkholm |
| 4,809,312 A | 2/1989 | Annis |
| 4,817,121 A | 3/1989 | Shimizu |
| 4,819,256 A | 4/1989 | Annis |
| 4,821,023 A | 4/1989 | Parks |
| 4,825,454 A | 4/1989 | Annis |
| 4,839,913 A | 6/1989 | Annis |
| 4,841,555 A | 6/1989 | Doi |
| 4,845,769 A | 7/1989 | Burstein |
| 4,864,142 A | 9/1989 | Gomberg |
| 4,870,670 A | 9/1989 | Geus |
| 4,884,289 A | 11/1989 | Glockmann |
| 4,890,310 A | 12/1989 | Umetani |
| 4,893,015 A | 1/1990 | Kubierschky |
| 4,894,619 A | 1/1990 | Leinonen |
| 4,899,283 A | 2/1990 | Annis |
| 4,961,214 A | 10/1990 | Van |
| 4,974,247 A | 11/1990 | Friddell |
| 4,979,137 A | 12/1990 | Gerstenfeld |
| 4,995,066 A | 2/1991 | Harding |
| 5,007,072 A | 4/1991 | Jenkins |
| 5,022,062 A | 6/1991 | Annis |
| 5,033,073 A | 7/1991 | Friddell |
| 5,038,370 A | 8/1991 | Harding |
| 5,039,981 A | 8/1991 | Rodriguez |
| 5,044,002 A | 8/1991 | Stein |
| 5,084,619 A | 1/1992 | Pfeiler |
| 5,115,459 A | 5/1992 | Bertozzi |
| 5,120,706 A | 6/1992 | Weeks |
| 5,121,105 A | 6/1992 | Aittoniemi |
| 5,127,030 A | 6/1992 | Annis |
| 5,132,995 A | 7/1992 | Stein |
| 5,156,270 A | 10/1992 | Kachel |
| 5,179,581 A | 1/1993 | Annis |
| 5,181,234 A | 1/1993 | Smith |
| 5,182,764 A | 1/1993 | Peschmann |
| 5,212,720 A | 5/1993 | Landi |
| 5,224,144 A | 6/1993 | Annis |
| 5,243,693 A | 9/1993 | Maron |
| 5,247,561 A | 9/1993 | Kotowski |
| 5,253,283 A | 10/1993 | Annis |
| 5,260,982 A | 11/1993 | Fujii |
| 5,313,511 A | 5/1994 | Annis |
| 5,367,552 A | 11/1994 | Peschmann |
| 5,394,454 A | 2/1995 | Harding |
| 5,397,986 A | 3/1995 | Conway |
| 5,420,905 A | 5/1995 | Bertozzi |
| 5,430,787 A | 7/1995 | Norton |
| 5,463,224 A | 10/1995 | Burstein |
| 5,483,569 A | 1/1996 | Annis |
| 5,490,218 A | 2/1996 | Krug |
| 5,493,596 A | 2/1996 | Annis |
| 5,503,424 A | 4/1996 | Agopian |
| 5,524,133 A | 6/1996 | Neale |
| 5,528,656 A | 6/1996 | Annis |
| 5,572,121 A | 11/1996 | Beswick |
| 5,579,360 A | 11/1996 | Abdel-Mottaleb |
| 5,590,057 A | 12/1996 | Fletcher |
| 5,600,303 A | 2/1997 | Husseiny |
| 5,600,700 A | 2/1997 | Krug |
| 5,602,893 A | 2/1997 | Harding |
| 5,638,420 A | 6/1997 | Armistead |
| 5,642,393 A | 6/1997 | Krug |
| 5,642,394 A | 6/1997 | Rothschild |
| 5,660,549 A | 8/1997 | Witt |
| 5,666,393 A | 9/1997 | Annis |
| 5,692,028 A | 11/1997 | Geus |
| 5,692,029 A | 11/1997 | Husseiny |
| 5,696,806 A | 12/1997 | Grodzins |
| 5,699,400 A | 12/1997 | Lee |
| 5,763,886 A | 6/1998 | Schulte |
| 5,764,683 A | 6/1998 | Swift |
| 5,796,110 A | 8/1998 | An |
| 5,838,758 A | 11/1998 | Krug |

(56) References Cited

U.S. PATENT DOCUMENTS

| | | |
|---|---|---|
| 5,882,206 A | 3/1999 | Gillio |
| 5,892,840 A | 4/1999 | Jang |
| 5,910,973 A | 6/1999 | Grodzins |
| 5,930,326 A | 7/1999 | Rothschild |
| 5,940,468 A | 8/1999 | Huang |
| 5,966,422 A | 10/1999 | Dafni |
| 5,974,111 A | 10/1999 | Krug |
| 6,018,562 A | 1/2000 | Willson |
| 6,044,353 A | 3/2000 | Pugliese |
| 6,057,761 A | 5/2000 | Yukl |
| 6,081,580 A | 6/2000 | Grodzins |
| 6,094,472 A | 7/2000 | Smith |
| 6,137,895 A | 10/2000 | Al-Sheikh |
| 6,151,381 A | 11/2000 | Grodzins |
| 6,192,104 B1 | 2/2001 | Adams |
| 6,212,251 B1 | 4/2001 | Tomura |
| 6,236,709 B1 | 5/2001 | Perry |
| 6,249,567 B1 | 6/2001 | Rothschild |
| 6,269,142 B1 | 7/2001 | Smith |
| 6,272,206 B1 | 8/2001 | Bjorkholm |
| 6,278,115 B1 | 8/2001 | Annis |
| 6,282,264 B1 | 8/2001 | Smith |
| 6,298,603 B1 | 10/2001 | Diaz |
| 6,301,326 B2 | 10/2001 | Bjorkholm |
| 6,301,327 B1 | 10/2001 | Martens |
| 6,308,644 B1 | 10/2001 | Diaz |
| 6,315,308 B1 | 11/2001 | Konopka |
| RE37,467 E | 12/2001 | Brasch |
| 6,366,203 B1 | 4/2002 | Burns |
| 6,370,222 B1 | 4/2002 | Cornick |
| 6,375,697 B2 | 4/2002 | Davies |
| 6,393,095 B1 | 5/2002 | Robinson |
| 6,418,194 B1 | 7/2002 | McPherson |
| 6,421,420 B1 | 7/2002 | Grodzins |
| 6,442,233 B1 | 8/2002 | Grodzins |
| 6,459,761 B1 | 10/2002 | Grodzins |
| 6,459,764 B1 | 10/2002 | Chalmers |
| 6,473,487 B1 | 10/2002 | Le |
| 6,484,650 B1 | 11/2002 | Stomski |
| 6,507,278 B1 | 1/2003 | Brunetti |
| 6,546,072 B1 | 4/2003 | Chalmers |
| 6,552,346 B2 | 4/2003 | Verbinski |
| 6,553,096 B1 | 4/2003 | Zhou |
| 6,556,653 B2 | 4/2003 | Hussein |
| 6,567,496 B1 | 5/2003 | Sychev |
| 6,597,760 B2 | 7/2003 | Beneke |
| 6,610,977 B2 | 8/2003 | Megerle |
| 6,621,888 B2 | 9/2003 | Grodzins |
| 6,628,745 B1 | 9/2003 | Annis |
| 6,634,668 B2 | 10/2003 | Urffer |
| 6,653,588 B1 | 11/2003 | Gillard-Hickman |
| 6,665,373 B1 | 12/2003 | Kotowski |
| 6,674,367 B2 | 1/2004 | Sweatte |
| 6,707,879 B2 | 3/2004 | McClelland |
| 6,721,391 B2 | 4/2004 | McClelland |
| 6,742,301 B1 | 6/2004 | Schwarz |
| 6,745,520 B2 | 6/2004 | Puskaric |
| 6,749,207 B2 | 6/2004 | Nadeau |
| 6,754,304 B1 | 6/2004 | Kumakhov |
| 6,785,360 B1 | 8/2004 | Annis |
| 6,819,109 B2 | 11/2004 | Sowers |
| 6,819,241 B2 | 11/2004 | Turner |
| 6,839,403 B1 | 1/2005 | Kotowski |
| 6,848,826 B2 | 2/2005 | Marie |
| 6,870,791 B1 | 3/2005 | Caulfield |
| 6,876,719 B2 | 4/2005 | Ozaki |
| 6,879,657 B2 | 4/2005 | Hoffman |
| 6,891,381 B2 | 5/2005 | Bailey |
| 6,899,540 B1 | 5/2005 | Neiderman |
| 6,901,346 B2 | 5/2005 | Tracy |
| 6,911,907 B2 | 6/2005 | Kelliher |
| 6,952,163 B2 | 10/2005 | Huey |
| 6,965,340 B1 | 11/2005 | Baharav |
| 6,967,612 B1 | 11/2005 | Gorman |
| 6,970,086 B2 | 11/2005 | Nelson |
| 6,970,087 B2 | 11/2005 | Stis |
| 6,990,175 B2 | 1/2006 | Nakashima |
| 7,053,785 B2 | 5/2006 | Akins |
| 7,092,485 B2 | 8/2006 | Kravis |
| 7,103,137 B2 | 9/2006 | Seppi |
| 7,110,493 B1 | 9/2006 | Kotowski |
| 7,110,925 B2 | 9/2006 | Pendergraft |
| 7,114,849 B2 | 10/2006 | Atzinger |
| 7,142,638 B2 | 11/2006 | Polichar |
| 7,162,005 B2 | 1/2007 | Bjorkholm |
| 7,164,747 B2 | 1/2007 | Ellenbogen |
| 7,185,206 B2 | 2/2007 | Goldstein |
| 7,203,276 B2 | 4/2007 | Arsenault |
| 7,257,189 B2 | 8/2007 | Modica |
| 7,265,709 B2 | 9/2007 | Fleisher |
| 7,286,634 B2 | 10/2007 | Sommer |
| 7,305,062 B2 | 12/2007 | Hambuchen |
| 7,305,063 B2 | 12/2007 | Heuscher |
| 7,330,529 B2 | 2/2008 | Kautzer |
| 7,333,587 B2 | 2/2008 | De |
| 7,356,115 B2 | 4/2008 | Ford |
| 7,365,672 B2 | 4/2008 | Keller |
| 7,400,701 B1 | 7/2008 | Cason |
| 7,418,077 B2 | 8/2008 | Gray |
| 7,460,636 B2 | 12/2008 | Ein-Gal |
| 7,476,023 B1 | 1/2009 | Canfield |
| 7,505,557 B2 | 3/2009 | Modica |
| 7,505,562 B2 | 3/2009 | Dinca |
| 7,551,709 B2 | 6/2009 | Schlomka |
| 7,551,715 B2 | 6/2009 | Rothschild |
| 7,561,666 B2 | 7/2009 | Annis |
| 7,593,506 B2 | 9/2009 | Cason |
| 7,593,510 B2 | 9/2009 | Rothschild |
| 7,639,866 B2 | 12/2009 | Pomero |
| 7,660,388 B2 | 2/2010 | Gray |
| 7,684,544 B2 | 3/2010 | Wilson |
| 7,783,004 B2 | 8/2010 | Kotowski |
| 7,796,394 B2 | 9/2010 | Wang |
| 7,796,733 B2 | 9/2010 | Hughes |
| 7,796,734 B2 | 9/2010 | Mastronardi |
| 7,806,589 B2 | 10/2010 | Tashman |
| 7,809,109 B2 | 10/2010 | Mastronardi |
| 7,817,776 B2 | 10/2010 | Agrawal |
| 7,826,589 B2 | 11/2010 | Kotowski |
| 8,135,112 B2 | 3/2012 | Hughes |
| 8,576,982 B2 * | 11/2013 | Gray et al. ..................... 378/57 |
| 8,638,904 B2 * | 1/2014 | Gray et al. ..................... 378/57 |
| 8,995,619 B2 | 3/2015 | Gray |
| 2002/0045152 A1 | 4/2002 | Viscardi |
| 2003/0012338 A1 | 1/2003 | Lienard |
| 2003/0171939 A1 | 9/2003 | Yagesh |
| 2003/0225612 A1 | 12/2003 | DeSimone |
| 2003/0229506 A1 | 12/2003 | Scott |
| 2004/0088584 A1 | 5/2004 | Shachar |
| 2004/0175018 A1 | 9/2004 | MacArthur |
| 2005/0276379 A1 | 12/2005 | Polichar |
| 2006/0262902 A1 | 11/2006 | Wattenburg |
| 2007/0009088 A1 | 1/2007 | Edic |
| 2007/0086564 A1 | 4/2007 | Bruder |
| 2007/0098142 A1 | 5/2007 | Rothschild |
| 2007/0235652 A1 | 10/2007 | Smith |
| 2008/0144777 A1 | 6/2008 | Wilson |
| 2008/0212742 A1 | 9/2008 | Hughes |
| 2009/0041186 A1 | 2/2009 | Gray |
| 2009/0082762 A1 | 3/2009 | Ormsby |
| 2009/0103686 A1 | 4/2009 | Rothschild |
| 2009/0116614 A1 | 5/2009 | Kotowski |
| 2009/0116617 A1 | 5/2009 | Mastronardi |
| 2009/0245462 A1 | 10/2009 | Agrawal |
| 2011/0017917 A1 | 1/2011 | Mastronardi |
| 2011/0096901 A1 | 4/2011 | Kotowski |
| 2011/0164726 A1 | 7/2011 | Mastronardi |
| 2011/0274249 A1 | 11/2011 | Gray |
| 2011/0274250 A1 | 11/2011 | Gray |
| 2011/0293072 A1 | 12/2011 | Kaminski |
| 2011/0299659 A1 | 12/2011 | Gray |

(56) References Cited

U.S. PATENT DOCUMENTS

FOREIGN PATENT DOCUMENTS

| CN | 101467071 | 6/2012 |
| CN | 101379415 | 7/2013 |
| EP | 0261984 A2 | 3/1988 |
| WO | 2009006044 | 1/2009 |
| WO | 2009082762 | 7/2009 |
| WO | 2009082762 A1 | 7/2009 |
| WO | 2011115923 A1 | 9/2011 |
| WO | 2011115930 A2 | 9/2011 |
| WO | 2011115934 A2 | 9/2011 |
| WO | 2011115935 A1 | 9/2011 |

OTHER PUBLICATIONS

ANSI, Radiation Safety for Personnel Security Screening Systems Using X-Rays, Apr. 3, 2002.

Daniel Strom, "Screening Individuals with Backscatter X-Ray Systems", Health Physics Society, Feb. 3, 2005.

Gerald J. Smith, 'Bodysearch Technology Uses X-ray Imaging to Remove Hazards and Humiliation from Personnel Searches', IEEE, 1995.

International Search Report, PCT/US2008/067619, Aug. 20, 2008, Rapiscan Security Products.

International Search Report, PCT/US2008/088345, Apr. 3, 2009, Rapiscan Security Products.

MSNBC, "Airports Seek Hi-Tech Security", Apr. 3, 2002.

Murray et al., 'Exploitation of X-Ray Technology for the Detection of Contraband-Aviation Security Applications', European Conference on Security and Detection, Apr. 28-30, 1997.

Rapiscan Security Products, Secure 1000 Brochure, 2002.

Rapiscan Security Products, Secure 1000 Concealed Object Detection System, Nov. 1998.

Rapiscan Systems Secure 1000 Case Study, London Heathrow Terminal 4, Fall 2004.

St. Bartholomew's Hospital, Radiation Safety Report on the Rapiscan Secure 1000 X-Ray System, Nov. 4, 2004.

International Search Report, PCT/US11/28411, Sep. 27, 2011, Rapiscan Systems Inc.

International Search Report, PCT/US11/28393, Jul. 8, 2011, Rapiscan Systems Inc.

International Search Report, PCT/US11/28413, Jul. 22, 2011, Rapiscan Systems Inc.

First Office Action for Chinese Application No. 2011800241163, Nov. 2014.

First office action for Chinese Application No. CN 201180024005.2, dated Jun. 23, 2014.

International Search Report, PCT/US11/28403, Oct. 11, 2011, Rapiscan Systems Inc.

\* cited by examiner

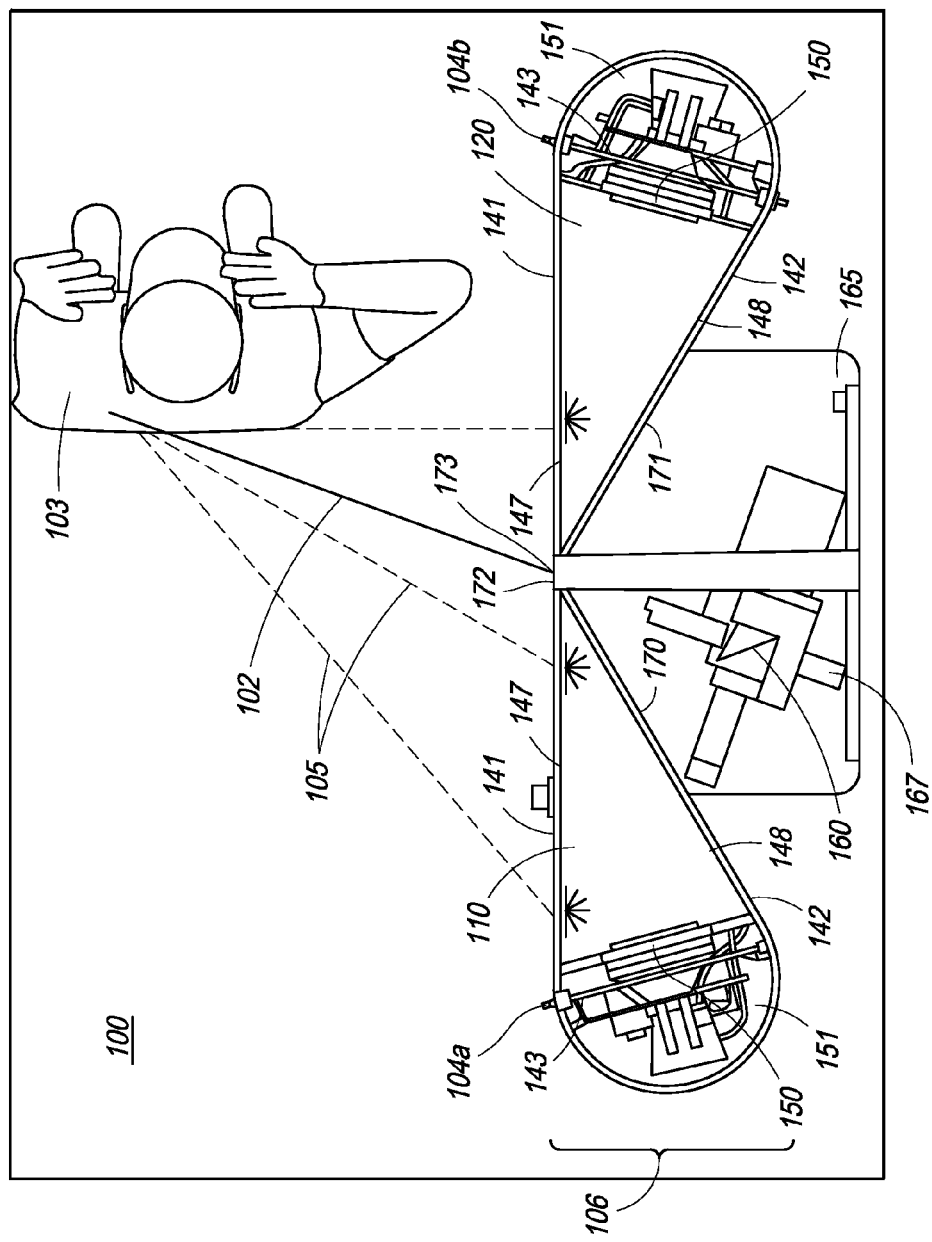

Table 1

| ITEM | PART NO. | QTY | MANUF PART NO. | MANF ALT | RECCOM DIST. | DESCRIPTION | UOM |
|---|---|---|---|---|---|---|---|
| 33 | 3094604-2 | 2 | | | | Cable Kit, Cat5e FTP Patch, Lg 1.0M | EA |
| 32 | 3094604-1 | 1 | | | | Cable Kit, Cat5e FTP Patch, Lg 0.5M | EA |
| 31 | 2194604-3 | 1 | | | | Cable Kit, Detector Tower PMT Power, Lg 37 inch | EA |
| 30 | 2194604-1 | 1 | | | | Cable Kit, Detector Tower PMT Power, Lg 20 inch | EA |
| 29 | 2194604-2 | 1 | | | | Cable Kit, Detector Tower PMT Power, Lg 34 inch | EA |
| 28 | 2194604-4 | 1 | | | | Cable Kit, Detector Tower PMT Power, Lg 50 inch | EA |
| 27 | 2194605-1 | 1 | | | | Cable Kit, Coax Detector Tower PMT Data, Lg 20 inch | EA |
| 26 | 2194605-2 | 1 | | | | Cable Kit, Coax Detector Tower PMT Data, Lg 36 inch | EA |
| 25 | 3494885 | 1 | | | | Plug, Connector, Corner Cover | EA |
| 24 | SW08-0000 | 42 | | | | Washer Flat #8 Regular Patte | EA |
| 21 | 8594836 | 22 | | | | Screw 10-32 X 3/4" Lg Soc Button HD SS | EA |
| 20 | 8594835 | 22 | | | | Bonded Washer #10, AL, W/NPR Backed | EA |
| 18 | 8594821 | 17 | | | | Screw Flat Socket Cap 1/4-20 X 1/2" Lg | EA |
| 15 | 8594818 | 6 | | | | Screw Flat Socket Cap 8-32 X 1/2" Lg | EA |
| 13 | 8510712 | 22 | | | | Washer Lock 10-32 SS | EA |
| 12 | 8510711 | 18 | | | | Washer Flat 10-32 SS | EA |
| 11 | 4094843 | 1 | | | | Connector Closure Cover, Secure 1000 MP | EA |
| 10 | 4094841 | 1 | | | | Connector, Corner Cover, Detector Tower Secure 1000 MP | EA |
| 9 | 4094781 | 1 | | | | PMT Mounting Plate Detector Assy Secure 1000 MP | EA |
| 8 | 5794776 | 12.5 | | | | Seal Detector Assy Secure 1000 MP | EA |
| 7 | 4094775 | 2 | | | | Trim Plate Detector Assy Secure 1000 MP | EA |
| 6 | 4094774 | 2 | | | | Handle, Detector Assy, Secure 1000 MP | EA |
| 5 | 4094773 | 1 | | | | Closure Cover Detector Assy Secure 1000 MP | EA |
| 4 | 4094772 | 1 | | | | Corner Cover Detector Tower Secure 1000 MP | EA |
| 3 | 2394770 | 1 | | | | Detector Tower, Detector Assy, Secure 1000 MP | EA |
| 2 | 2394771 | 4 | | | | PMT Assy Detector Assy Secure 1000 MP | EA |
| 1 | 2294726 | 1 | | | | 4 Channel Card, Detector Assy, Secure 1000 MP | EA |

PARTS LIST

FIG. 2G

Table 2

| ITEM | PART NO. | QTY | MANUF PART NO. | MANF ALT | RECCOM DIST. | DESCRIPTION | UOM |
|---|---|---|---|---|---|---|---|
| 57 | 2194605-4 | 1 | | | | Cable Kit, Coax Detector Tower PMT Data | EA |
| 56 | 2194605-3 | 1 | | | | Cable Kit, Coax Detector Tower PMT Data | EA |
| 55 | 85104498 | 4 | | | | KEP Nut 4-40, 3/32" LG, SS | EA |
| 54 | 85104499 | 4 | | | | Screw, 4-40 X 3/8" LG, SS, PH Pan HD | EA |
| 53 | 85104500 | 1 | | | | Screw, 1/4" - 20x 1 1/2" LG Flat, Soc HD, SS | EA |
| 52 | 85104501 | 1 | | | | KEP Nut 1/4"-20, SS | EA |
| 51 | 21104506 | 4 | | | | Grounding Wire, PMT Boards | EA |
| 50 | 211044476-2 | 2 | | | | Cable Assy, Ground Wire | EA |
| 49 | 211044476-1 | 1 | | | | Cable Assy, Ground Wire | EA |
| 48 | 85104502 | 42 | | | | KEP nut 8-32, 1/8" LG,SS | EA |
| 47 | 85104503 | 18 | | | | KEP Nut 10-32, 1/8" LG, SS | EA |
| 46 | 85104491 | 4 | | | | Screw 6-32 X 1/4" Lg PH Pan HD,SS | EA |
| 45 | 85104497 | 4 | | | | Standoff 6-32 X 3/4" Lg, SS | EA |
| 44 | 31104385 | 14 | | | | Cable Tie, Mounting Base, Aluminum | EA |
| 43 | 34104374 | 1 | | | | Protection Cap Communication Com | EA |
| 42 | SF10-3208 | 12 | | | | Screw, FHPS 10-32, 1/2" LG | EA |
| 41 | 31104262 | 8 | | | | Clamp, HV Cable Assy, Secure 1000MP | EA |
| 40 | 8800010 | 1 | | | | Label Earth | EA |
| 39 | 8800015 | 2 | | | | Label High Voltage Warning | EA |
| 38 | 8594887 | 8 | | | | Screw Flat Socket Cap 8-32 X 1.0" Lg | EA |
| 37 | 2994867 | 1 | | | | Firmware, 4 ChannelBoard, Detector Assy | EA |
| 36 | 2994866 | 1 | | | | Firmware, Communication, Detector Assy | EA |
| 35 | 2194619 | 1 | | | | Cable Assy, PWR & Data Tower | EA |
| 34 | 3094604-3 | 1 | | | | Cable Kit, Cat5e FTP Patch, Lg 2.0M | EA |

PARTS LIST

FIG. 2H

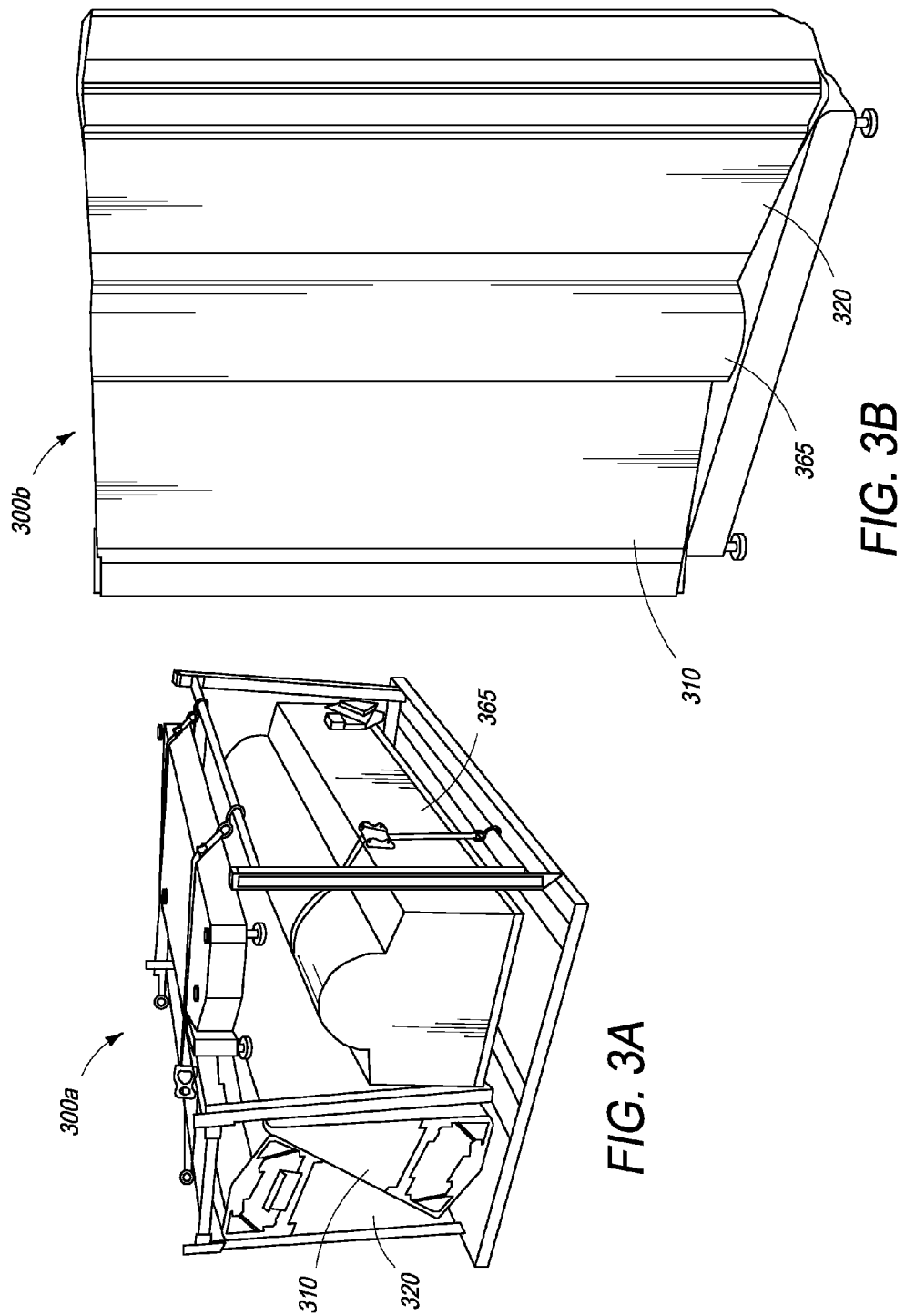

PERSONNEL SCREENING SYSTEM

CROSS-REFERENCE TO RELATED APPLICATIONS

The present application relies on U.S. Provisional Patent Application No. 61/313,772, filed on Mar. 14, 2010, for priority, which is herein incorporated by reference in its entirety.

The present application also relies on U.S. Provisional Patent Application No. 61/423,585, filed on Dec. 15, 2010, for priority, which is herein incorporated by reference in its entirety.

In addition, the present application relies on U.S. Provisional Patent Application No. 61/423,582, filed on Dec. 15, 2010, for priority, which is herein incorporated by reference in its entirety.

In addition, the present application relies on U.S. Provisional Patent Application No. 61/423,586, filed on Dec. 15, 2010, for priority, which is herein incorporated by reference in its entirety.

Further, the present application is a continuation-in-part of U.S. patent application Ser. No. 12/887,510, entitled "Security System for Screening People" and assigned to the applicant of the present invention, which is a continuation of U.S. Pat. No. 7,826,589, of the same title and also assigned to the applicant of the present invention, both of which are herein incorporated by reference in their entirety.

Further, the present application is a continuation-in-part of U.S. patent application Ser. No. 12/849,987, entitled "Personnel Screening System with Enhanced Privacy" and assigned to the applicant of the present invention, which is a continuation of U.S. Pat. No. 7,796,733, of the same title and also assigned to the applicant of the present invention, both of which are herein incorporated by reference in their entirety.

FIELD OF THE INVENTION

The invention relates generally to security systems for screening threats contained on persons, and more specifically, to a personnel screening system that comprises modular components for improved portability.

BACKGROUND OF THE INVENTION

Radiation based systems for screening people and in use today at transit points, such as airports, courthouses, etc., are generally portal systems that are bulky and not conducive for portable applications. Unfortunately, such prior art screening systems are not compact enough (example, have heavy back-end cables and wires for connecting the photomultiplier tubes to a centralized analog-to-digital conversion and power station) and are often difficult and time-consuming to use and/or transport.

Also, security systems are presently limited in their ability to detect contraband, weapons, explosives, and other dangerous objects concealed under clothing. Metal detectors and chemical sniffers are commonly used for the detection of large metal objects and certain types of explosives, however, a wide range of dangerous objects exist that cannot be detected using these devices. Plastic and ceramic weapons increase the types of non-metallic objects that security personnel are required to detect. Manual searching of subjects is slow, is inconvenient, and would not be well tolerated by the general public, especially as a standard procedure in high traffic centers, such as at airports.

It is known in the art that images of various types of material can be generated using X-ray scattering. The intensity of scattered X-rays is related to the atomic number (Z) of the material scattering the X-rays. In general, for atomic numbers less than 25, the intensity of X-ray backscatter, or X-ray reflectance, decreases with increasing atomic number. Images are primarily modulated by variations in the atomic number of the subject's body. Low-Z materials present a special problem in personnel inspection because of the difficulty in distinguishing the low-Z object from the background of the subject's body which also has low-Z.

Known prior art X-ray systems for detecting objects concealed on persons have limitations in their design and method that prohibit them from achieving low radiation doses, which is a health requirement, or prevent the generation of high image quality, which are prerequisites for commercial acceptance. An inspection system that operates at a low level of radiation exposure is limited in its precision by the small amount of radiation that can be directed towards a person being searched. X-ray absorption and scattering further reduces the amount of X-rays available to form an image of the person and any concealed objects. In prior art systems this low number of detected X-rays has resulted in unacceptably poor image quality.

This problem is even more significant if an X-ray inspection system is being used in open venues such as stadiums, shopping malls, open-air exhibitions and fairs, etc. At such venues, people can be located both proximate to and/or at a distance from the machine. If a person being scanned is not very close to the X-ray machine, the resultant image may not be clear enough since the amount of radiation reaching the person is very low. This limits the range of scanning of the system to a few feet from the front of the machine. If, however, a person being scanned is too close to the X-ray machine, the amount of radiation impinging on the person may not be safe.

Further, X-ray screening systems deployed at airports in the United States of America (U.S.A.), for performing automatic threat detection, have to comply with guidelines set by the Transportation Security Administration (TSA). Current TSA guidelines require being capable of scanning a person at least 6 feet 6 inches tall from elbow to elbow which translates into a scanning width of at least 103 centimeters. Also, given the increasing rush at the airports, a screening system deployed at an airport or other such heavy throughput areas must provide a fast scanning time, preferably ranging around 10 seconds per scan. Yet further, a screening system should preferably be compliant with laws governing disabled persons. In the U.S.A the screening systems must be compliant with the regulations set forth in the Americans with Disabilities Act (ADA).

Therefore, there is a need for a compact radiographic detector/source screening system that has improved detection efficiency, is light yet sufficiently rugged and can be easily unassembled for transportation and then is simple to reassemble at a site.

Also is required a screening system that may be deployed easily by virtue of modularity, smaller size, reduced weight and rapid assembly; while at the same time provide a higher scan speed (higher personnel throughput), and the latest processing electronics.

There is also a need for a radiographic screening system that provides good resolution as well as large range of view and fast scanning speed, while keeping the radiation exposure within safe limits. That is, the system should not only be safe for people at close distances, but also provide a good resolution and penetration at standoff distances. In particular, conventional systems have been unable to generate the requisite field of view (scanning a person of a predefined height and width), at a predefined distance from the inspection system, at the required scan speed at an acceptable radiation exposure level to yield an acceptable resolution level.

SUMMARY OF THE INVENTION

In one embodiment, the present specification discloses an inspection system for detecting objects being carried by a stationary person comprising a first detection system configured to detect radiation scattered from said person, wherein said first detection system is configured to generate electronic signals responsive to the detected radiation; a second detection system configured to detect radiation scattered from said person, wherein said second detection system is configured to generate electronic signals responsive to the detected radiation; an X-ray source positioned in an enclosure between said first detection system and said second detection system, wherein said X-ray source is coupled to a beam chopper, having a diameter, and configured to emit an X-ray beam through a space between said first detection system and said second detection system, wherein said space is defined by a width ranging from ½ to 2 times the diameter of the beam chopper; and a processing system for analyzing the electronic signals generated by the first detection system and the second detection system and for generating an image on a display.

Optionally, the beam chopper is a wheel and wherein said wheel has three slits and wherein each slit positioned 120 degrees apart from an adjacent slit. The slits are aligned with at least two parallel collimator slits and wherein X-rays emitted from the X-ray source conically illuminate the collimator slits to generate at least two parallel scanning beams interleaved in time. The beam chopper comprises a hollow cylinder having at least one helical aperture. The first detection system is contained within a first enclosure and wherein the second detection system is contained within a second enclosure. The first enclosure is physically separate from, and independent of, said second enclosure. The X-ray source enclosure is physically separate from, and independent of, the first and second enclosures. Each of the first, second, and third enclosures weigh less than 88 pounds. The third enclosure may be detachably connected to the first enclosure and the second enclosure. Each of the first, second, and third enclosures may be detachably connected to a frame. The beam chopper comprises a disk chopper that is configured to be rotated by a motor. The speed of the chopper wheel is dynamically controlled by a controller to optimize a scan velocity of the X-ray beam.

Optionally, the first enclosure comprises a first side defined by a planar surface having an exterior surface facing the person and an interior surface, wherein the first side is configured to receive the radiation scattered from the person; a second side in an acute angular relationship with said first side, wherein said second side is defined by a planar surface having an interior surface adapted to receive radiation passing through the first side and wherein said second side is configured to only receive radiation after it passes through said first side; a first substrate positioned on the interior surface of the first side, wherein the first substrate further comprises an active area for receiving and converting said radiation into light; a second substrate positioned on the interior surface of the second side, wherein the second substrate further comprises an active area for receiving and converting said radiation into light; and at least one photodetector having a light responsive area and a non-light responsive area, wherein the light responsive area is positioned to receive the light emitted from the first substrate and the second substrate.

Optionally, the radiation comprises X-ray photons and wherein said first substrate detects 30-60% of the X-ray photons impinging on said first side. The second substrate detects 10-30% of the X-ray photons impinging on said first side. The X-ray source generates a vertical beam spot pattern by pivoting from a first point to a second point and wherein said pivoting is centered around a predefined point of rotation. The X-ray source and the beam chopper are coupled to a surface configured to tilt vertically in relation to a guide member and in response to a motor. The X-ray source is coupled to a vertical elevating mechanism wherein said elevating mechanism is coupled to a weight configured to counterbalance the X-ray source. The X-ray source is coupled to a vertical elevating mechanism wherein said elevating mechanism is coupled to at least one lifting belt. The X-ray source is coupled to a vertical elevating mechanism wherein said elevating mechanism is coupled to a gear reducer and motor and wherein said elevating mechanism is not coupled to a counterbalancing weight.

In another embodiment, the present specification discloses an inspection system for detecting objects being carried by a stationary person having a height equal to or less than 6 feet 8 inches and a width equal to or less than 45 inches comprising: a first detection system configured to detect radiation scattered from said person, wherein said first detection system is configured to generate electronic signals responsive to the detected radiation; a second detection system configured to detect radiation scattered from said person, wherein said second detection system is configured to generate electronic signals responsive to the detected radiation; an X-ray source positioned in an enclosure, having a surface, between said first detection system and said second detection system, wherein said X-ray source is coupled to a beam chopper and configured to generate a field of view capable of scanning the height and the width of said person when said person is positioned no more than one foot from the surface of the enclosure; and a processing system for analyzing the electronic signals generated by the first detection system and the second detection system and for generating an image on a display, wherein said image has sufficient resolution to visually differentiate between the person's body and explosive material. Sufficient resolution may be defined as an image resolution sufficient to allow for the visual differentiation between low Z materials, such as materials with an effective atomic number of less than 8, and human body tissue. Sufficient resolution may also be defined by those imaging parameters provided in U.S. Pat. Nos. 7,110,493 and 5,181,234, both of which are incorporated herein by reference.

Optionally, the X-ray source is coupled to a beam chopper wheel and wherein said wheel has three slits with each slit being positioned 120 degrees apart from an adjacent slit. The slits are aligned with at least two parallel collimator slits and wherein X-rays emitted from the X-ray source conically illuminate the collimator slits to generate at least two parallel scanning beams interleaved in time. The X-ray source is coupled to a beam chopper and wherein said beam chopper comprises a hollow cylinder having at least one helical aperture. The first detection system is contained within a first enclosure and wherein the second detection system is contained within a second enclosure. The first enclosure is physically separate from, and independent of, said second enclosure. The X-ray source enclosure is physically separate from, and independent of, the first and second enclosures. Each of the first, second, and third enclosures weigh less than 88 pounds. The third enclosure may be detachably connected to the first enclosure and the second enclosure. Each of the first, second, and third enclosures may be detachably connected to a frame. The X-ray source is coupled to a beam chopper and wherein the beam chopper comprises a disk chopper that is configured to be rotated by a motor. The speed of the chopper wheel is dynamically controlled by a controller to optimize a scan velocity of the X-ray beam.

Optionally, the first enclosure comprises: a first side defined by a planar surface having an exterior surface facing the person and an interior surface, wherein the first side is configured to receive the radiation scattered from the person; a second side in an acute angular relationship with said first side, wherein said second side is defined by a planar surface having an interior surface adapted to receive radiation passing through the first side and wherein said second side is configured to only receive radiation after it passes through said first side; a first substrate positioned on the interior surface of the first side, wherein the first substrate further comprises an active area for receiving and converting said radiation into light; a second substrate positioned on the interior surface of the second side, wherein the second substrate further comprises an active area for receiving and converting said radiation into light; and at least one photodetector having a light responsive area and a non-light responsive area, wherein the light responsive area is positioned to receive the light emitted from the first substrate and the second substrate.

The radiation comprises X-ray photons and wherein said first substrate detects 30-60% of the X-ray photons impinging on said first side. The second substrate detects 10-30% of the X-ray photons impinging on said first side. The X-ray source generates a vertical beam spot pattern by pivoting from a first point to a second point and wherein said pivoting is centered around a predefined point of rotation. The X-ray source and a beam chopper are coupled to a surface configured to tilt vertically in relation to a guide member and in response to a motor. The X-ray source is coupled to a vertical elevating mechanism wherein said elevating mechanism is coupled to a weight configured to counterbalance the X-ray source. The X-ray source is coupled to a vertical elevating mechanism wherein said elevating mechanism is coupled to at least one lifting belt. The X-ray source is coupled to a vertical elevating mechanism wherein said elevating mechanism is coupled to a gear reducer and motor and wherein said elevating mechanism is not coupled to a counterbalancing weight.

In another embodiment, the present specification discloses an inspection system for detecting objects being carried by a stationary person having a height equal to or less than 6 feet 8 inches and a width equal to or less than 45 inches comprising: a first detection system configured to detect radiation scattered from said person, wherein said first detection system is configured to generate electronic signals responsive to the detected radiation; a second detection system configured to detect radiation scattered from said person, wherein said second detection system is configured to generate electronic signals responsive to the detected radiation; a radiation source positioned in an enclosure, having a surface, between said first detection system and said second detection system, wherein said radiation source is coupled to a beam forming apparatus and configured to generate a field of view capable of scanning the height and the width of said person when said person is positioned no more than one foot from the surface of the enclosure and further configured to conduct a scan of said person in less than 20 seconds while exposing said person to no more than 20 microrem of radiation; and a processing system for analyzing the electronic signals generated by the first detection system and the second detection system and for generating an image on a display, wherein said image has sufficient resolution to visually differentiate between the person's body and explosive material.

In another embodiment, the present specification discloses an inspection system for detecting objects being carried by a stationary person having a height equal to or less than 6 feet 8 inches and a width equal to or less than 45 inches comprising: a first detection system configured to detect radiation scattered from said person, wherein said first detection system is configured to generate electronic signals responsive to the detected radiation; a second detection system configured to detect radiation scattered from said person, wherein said second detection system is configured to generate electronic signals responsive to the detected radiation; a radiation source positioned in an enclosure, having a surface, between said first detection system and said second detection system, wherein said radiation source is coupled to a beam forming apparatus and configured to generate a field of view capable of scanning the height and the width of said person when said person is positioned no more than one foot from the surface of the enclosure; a controller for controlling said radiation source to conduct at least one scan of said person over a time period of no more than 20 seconds and to expose said person to no more than 20 microrem of radiation; and a processing system for analyzing the electronic signals generated by the first detection system and the second detection system and for generating an image on a display, wherein said image has sufficient resolution to visually differentiate between the person's body and explosive material.

Optionally, the controller is configured to control said radiation source to conduct one scan of said person in a period of no more than 10 seconds. The controller is configured to control said radiation source to expose said person to no more than 5 microrem of radiation. The radiation source is configured to generate a field of view capable of scanning a height equal to six feet, six inches or less and a width of 40.5 inches or less when said person is positioned no more than ten inches from the surface of the enclosure. The controller is configured to control said radiation source to conduct one scan of said person in a period of no more than 10 seconds and wherein the controller is configured to control said radiation source to expose said person to no more than 5 microrem of radiation.

BRIEF DESCRIPTION OF THE DRAWINGS

These and other features and advantages of the present invention will be appreciated, as they become better understood by reference to the following detailed description when considered in connection with the accompanying drawings, wherein:

FIG. 1 illustrates an exemplary X-ray backscatter system configuration, including a detection system and towers, for the screening system of the present invention;

FIG. 2G shows Table 1 comprising a first set of bill-of-materials with reference to corresponding item numbers marked in the views of FIGS. 2A through 2F;

FIG. 2H shows Table 2 comprising a second set of bill-of-materials with reference to corresponding item numbers marked in the views of FIGS. 2A through 2F;

FIG. 3A is an unassembled and packaged illustration of an exemplary modular X-ray backscatter system configuration, including detection system and towers, for the personnel screening system of the present invention;

FIG. 3B is an assembled illustration of the exemplary modular X-ray backscatter system configuration shown in FIG. 3A;

DETAILED DESCRIPTION OF THE INVENTION

Figure 2A:
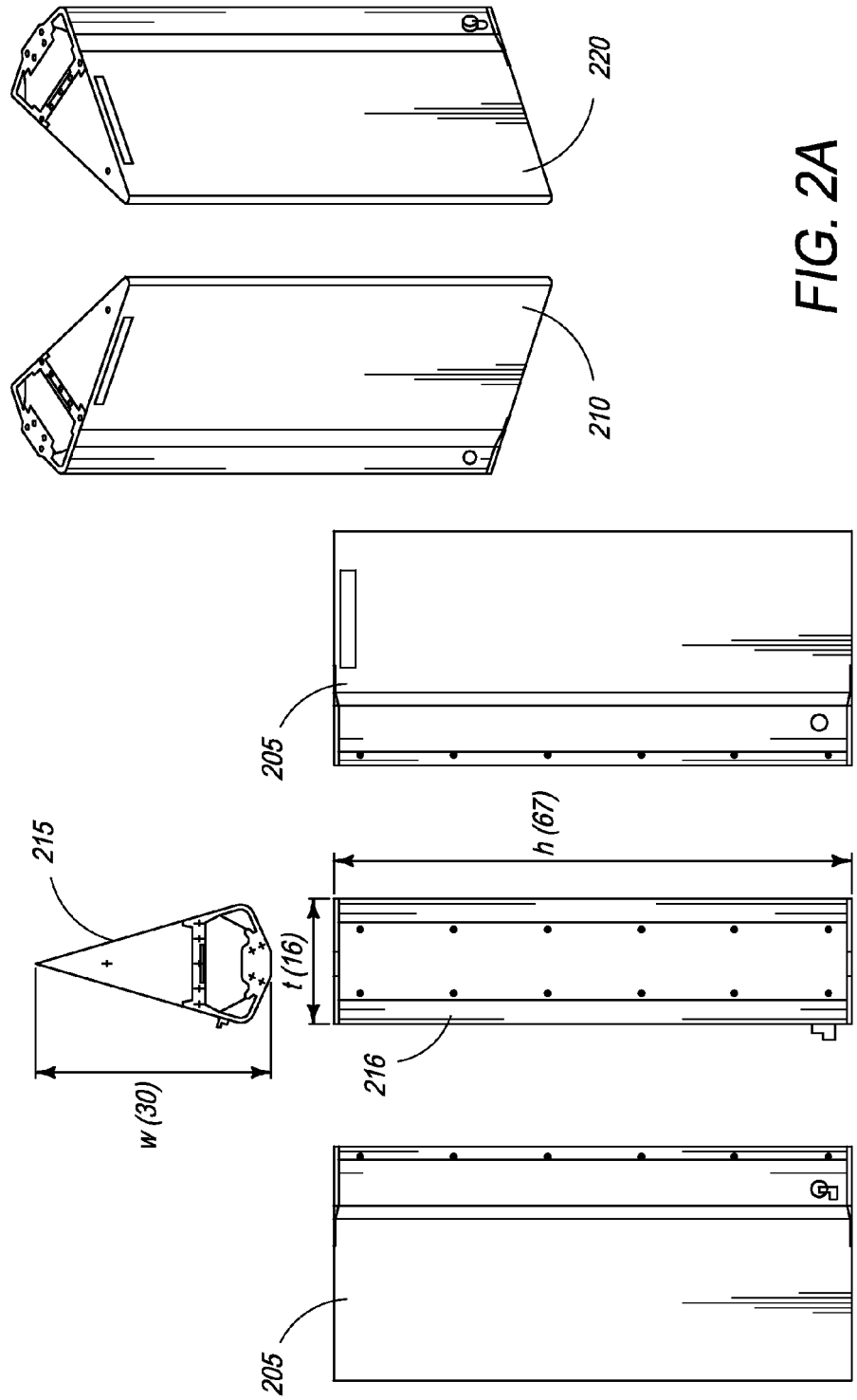
FIG. 2A shows multiple views of the detector towers in accordance with an embodiment of the present invention.

The present specification is directed towards personnel screening systems comprising modular components, including detector and source units. The modular components of the present invention allow for a compact, light and yet sufficiently rugged overall structure that can be disassembled for ease of transportation and is also simple to reassemble at a required site for inspection. The novel modular architecture of the screening system of the present invention also allows for the modular components to be fabricated separately and be quickly snapped on for assembly. Similarly, the modular components can be easily disassembled for ease of service access to the selective components and/or for packaging for subsequent transportation.

The present specification is also an improved method for screening individuals at security locations without exposing individuals to high radiation and retaining the efficiency of the screening process. The disclosed system allows for maximum threat detection performance and image clarity irrespective of the distance of the individuals from the screening system. Thus, in one embodiment, the present invention is a modular imaging apparatus for detecting a concealed object carried on a human body under inspection.

In X-ray backscatter systems for detecting concealed objects, a pencil beam of X-rays traverses over the surface of the body of a person being examined. X-rays that are scattered or reflected from the subject's body are detected by a detector such as, for example, a scintillator and photomultiplier tube combination. The resultant signal produced by the X-ray detector is then used to produce a body image, such as a silhouette, of the subject and any concealed objects carried by the subject.

In one embodiment, the present invention comprises a first module, further comprising a housing to enclose a radiation source and collimation means for directing radiation towards said human body, wherein said housing comprises first and second angled sides.

In one embodiment, a radiographic image is formed using any available radiation imaging technique for "body imaging" such as, but not limited to X-ray scattering, infrared imaging, millimeter wave imaging, RF imaging, radar imaging, holographic imaging, CT imaging, and MRI. Any "body imaging" system that has the potential for displaying body detail may be employed. In one embodiment, any photodetectable radiation or any radiation source with a light beam may be employed in the present invention.

In one embodiment, the present invention comprises a second module, further comprising first and second tear-drop detector towers, wherein each said tower further comprises first, second and third side areas connected to each other at an angle; and wherein the first side area comprises a first scintillator screen facing the human body under inspection to detect radiation backscattered from said human body and the second side area comprises a second scintillator screen inside each said tower to detect radiation backscattered from said human body but transmitted through the said first scintillator screen without detection;

In one embodiment, the present invention comprises a first and second set of plurality of photomultiplier tubes enclosed in the interior of each of the said first and second detector towers and placed proximate to the said third side area generating signals representative of the intensity of the radiation backscattered from said human body and detected at the said first and second scintillator screens.

In one embodiment, the present invention comprises a third module, further comprising first and second substantially semi-circular housing to enclose back-end electronics of the said first and second set of plurality of photomultiplier tubes.

In one embodiment, the present invention comprises a front-end strip separating the said first and second detector towers and comprising a limited opening to enable radiation from said radiation source to pass through and impinge the said human body.

In one embodiment, the present invention comprises a processor for processing the said signals from the said first and second set of plurality of photomultiplier tubes and generating an image on a display means.

In another embodiment, the present invention is method for using a modular imaging apparatus for detecting a concealed object carried on a human body under inspection, the method comprising the steps of operating a radiation source and collimation means, enclosed in a housing and forming a first module, for directing radiation towards said human body, wherein said housing comprises first and second angled sides and detecting, at a second module, radiation backscattered from said human body at a first scintillator screen and also detecting at a second scintillator screen radiation backscattered from said human body but transmitted through the said first scintillator screen without detection; wherein the second module comprises first and second tear-drop detector towers, wherein each said tower further comprises first, second and third side areas connected to each other at an angle; and wherein the first side area comprises the said first scintillator screen facing the said human body and the second side areas comprises the said second scintillator screen.

In one embodiment, the method also comprises the step of generating a signal representative of the intensity of the radiation backscattered from said human body and detected at the said first and second scintillator screens, using a first and second set of plurality of photomultiplier tubes enclosed in the interior of each of the said first and second detector towers and placed proximate to the said third side area.

In one embodiment, the method also comprises the step of processing the signals from the said first and second set of plurality of photomultiplier tubes and generating an image on a display means; wherein back-end electronics of the said first and second set of plurality of photomultiplier tubes are enclosed in first and second substantially semi-circular housings that form a third module; and a front-end strip separates the said first and second detector towers and comprises a limited opening to enable radiation from said radiation source to pass through and impinge the said human body.

In one embodiment of the present invention, 40% of the backscattered radiation impinging the first scintillator screen is detected by the said first scintillator screen and about 20% of the remaining backscattered radiation is detected by the said second scintillator screen.

In one embodiment, the collimation means is a chopper wheel. In one embodiment, the first and second detector towers are separated by the said front-end strip by a distance ranging from ½ to 2 times the diameter of the chopper wheel.

In one embodiment, the back-end electronics comprises first and second signal processing boards located in proximity to the said first and second set of plurality of photomultiplier tubes, wherein the said first and second signal processing boards each mount at least one analog to digital conversion card and a power supply module.

In one embodiment, the system of present invention requires a subject under inspection to assume only one position and uses a single source with a single group of detectors, circuits and processor to generate two separately processed scanning beams and associated images.

In one embodiment, the system of present invention is a walk-through inspection system that uses a single source with a single group of detectors, circuits and processor to generate two separately processed scanning beams and associated images.

In another embodiment, the system operates in a dual-source mode but uses a single group of detectors, circuits and processor.

The system allows for detection of threats by efficient imaging of explosive materials such as dynamite, C-4, as well as ceramics, graphite fibers, plastic containers, plastic weapons, glass vials, syringes, packaged narcotics, bundled paper currency, and even wooden objects.

In one embodiment, the X-ray backscatter imaging system of the present invention is designed such that it is optimized for near-real time imaging of people or objects with an interrogating radiation beam, while they are in motion. The system is also capable of automatically detecting threats by processing detection algorithms on the image data in near real-time.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 illustrates an exemplary X-ray backscatter system configuration for the novel modular screening system 100 of the present invention. Referring to FIG. 1, an X-ray source 160 is enclosed in a modular housing 165 and is employed to generate a narrow pencil beam 102 of X-rays directed towards the subject under inspection 103.

In one embodiment, pencil beam 102 is formed with the integration of an X-ray tube and a beam chopping mechanism 167. The pencil beam 102 is rastered either horizontally or vertically across the subject. This rastering is the result of the beam chopping mechanism by only allowing a minimal exit aperture for the x-ray beam to project. If a chopper wheel is employed, as described below, the exit aperture is 1 mm in diameter resulting in a X-ray beam that has diverged to about 7 mm. In one embodiment, subject 103 is a human. As the target (person being scanned) 103 poses in front of or walks by the screening system 100, the resultant pencil beam 102 hits the target, whereby at least a portion of the X-rays are backscattered. Exemplary embodiments of beam chopping mechanism 167 are described in greater detail below.

It should be understood to those of ordinary skill in the art that any number of ionizing radiation sources may be used, including but not limited to gamma radiation, electromagnetic radiation, and ultraviolet radiation. Preferably the X-ray energies employed are between 30 kV and 100 kV.

In one embodiment, sensors 104a and 104b are employed to detect the presence of a person as he or she poses in front of or walks through the screening system.

At least a portion of the scattered X-rays 105 impinges upon detector arrangement 106. In one embodiment, detector arrangement 106 in the screening system of the present invention comprises first and second detector enclosures 110 and 120 for enabling detection. In one embodiment, first and second detector enclosures 110 and 120 are embodied in the form of modular detector towers, which comprise at least one scintillator screen. In another embodiment, first and second detector enclosures 110 and 120 are modular detector towers that comprise at least two detector screens. In alternate embodiments, the detector enclosures may comprise any number of arrangements including, but, not limited to a plurality of detector screens. U.S. patent application Ser. No. 12/262,631, entitled "Multiple Screen Detection System" and assigned to the applicant of the present invention, is herein incorporated by reference. In addition, U.S. Provisional Patent Application No. 61/313,733, entitled "Multiple Screen Detection Systems" and filed on Mar. 14, 2010, is herein incorporated by reference in its entirety.

As shown in FIG. 1, detector towers 110 and 120 each comprise first side area 141, second side area 142, and third side area 143 that are connected to each other at an angle to form a triangular cross-section. The first side area 141 comprises screen 147 and faces subject 103 under inspection. The second side area 142 comprises a second screen 148 in the interior of the towers. In one embodiment, screens 147, 148 are relatively thick $CaWO_4$ scintillator screens that have a relatively short decay time of 10 microseconds that allows for the rapid scanning of the radiation beam with minimal image degradation. The $CaWO_4$ screen, in one embodiment, is capable of detecting approximately 70% of the backscattered or transmitted radiation, and thus, produces approximately 250 usable light photons per 30 keV X-ray. Additionally, the use of a thicker screen enables the detection of more of the radiation incident upon the detector at the expense of lower light output. In one embodiment, the areal density of the screen is 80 milligrams per square centimeter.

In one embodiment, to fasten the detector towers to the base, large diameter shoulder bolts are pre-fastened to the base, such that the detector towers can be "twisted" and locked onto the base. Once the radiation source and housing is attached to the base, the detector towers cannot be moved and twisted off. Radiation housing area 165 comprises first angled side 170 and second angled side 171 such that they easily abut and coincide with the sides 142 of the detector towers 110 and 120, when the detector towers and the radiation source housing are integrated or assembled together. A front-end side strip 172 facing the subject 103 comprises an opening 173 through which X-ray beam 102 passes before striking subject 103. Limited opening 173 aids in the reduction of electromagnetic interference and radiation noise. The side strip 172 also acts as a separator for the two detector towers such that the two detector towers are assembled symmetrically around incident X-ray pencil beam 102 to detect backscattered X-rays 105 and provide an electronic signal characteristic of the X-ray reflectance.

In one embodiment, the detector towers 110 and 120 are spaced apart by the strip 172 such that the chopper wheel or other beam collimation means is in the middle of the two towers. The two towers 110, 120 are separated by a distance 'd', that in one embodiment ranges from ½ to 2 times the diameter of the chopper wheel. The distance 'd' defines the field of view for the X-ray source and is optimized for a sufficient field of view while preventing overexposure of the detectors.

According to one embodiment of the present invention, detector towers 110, 120 and radiation housing 165 are of composite walls or any other similar non-conductive material evident to those of ordinary skill in the art that provides an optimization of a sturdy yet light overall structure. Specifically, housing the back-end electronics, wires and cables associated with the photomultipliers and radiation source within composite walls creates a Faraday cage, thus substantially reducing electromagnetic interference.

In an embodiment of the present invention, detector towers 110, 120 also comprise lighting means, such as LEDs, on the periphery or any one of the edges of the front area 141 for illumination depicting that the screening system is on and/or screening is in progress. Each of the towers 110, 120 comprises photomultiplier tubes 150 that are placed in the interior of the towers proximate to third side area 143. The back-end electronics of the photomultiplier tubes 150 is housed in the substantially semi-circular housing 151.

FIGS. 2A through 2F show structural details of the detector towers in accordance with various embodiments of the present invention. FIGS. 2G and 2H show the bill-of-materials with reference to corresponding item numbers marked in the views of FIGS. 2A through 2F. Specifically, FIG. 2A shows perspective views of identical detector towers 210 and 220 along with their respective front views 205, top view 215 and side view 216. In one embodiment, the towers have a height 'h' of 67 inches, lateral width 'w' of 30 inches and maximum thickness 't' of 16 inches.

Figure 2B:
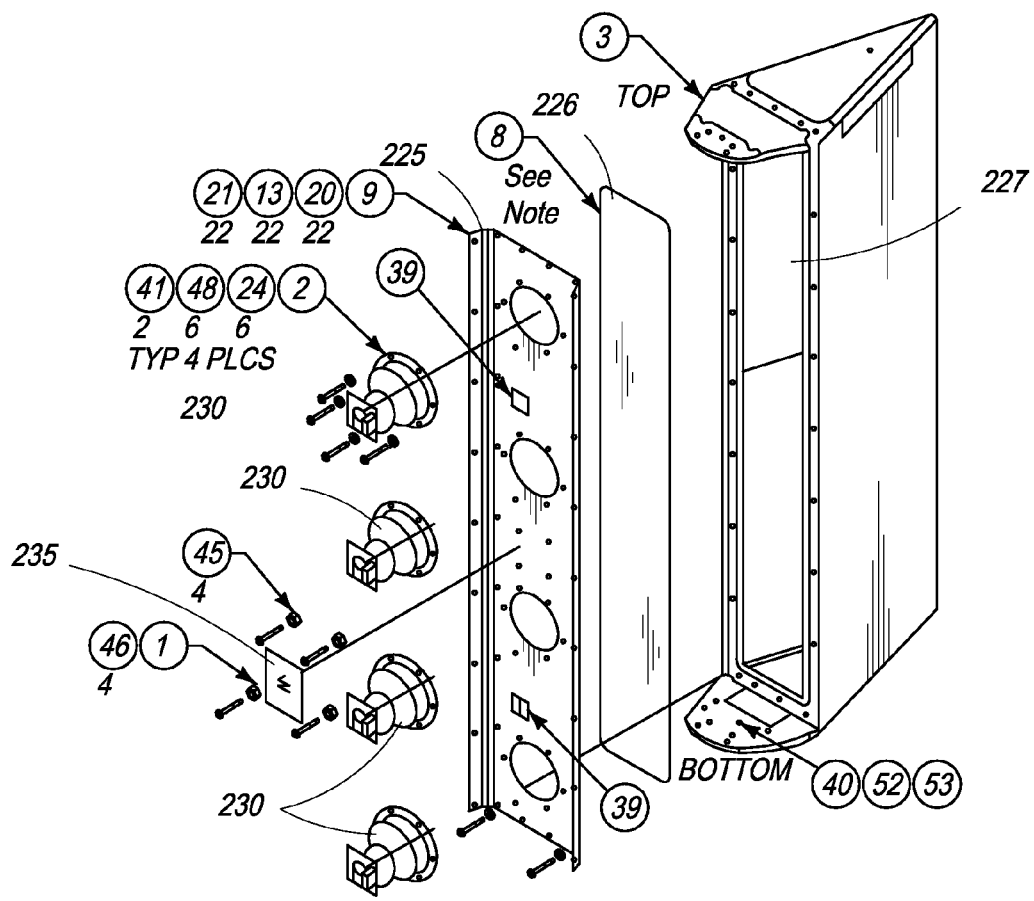
FIG. 2B shows an exploded view of the photomultiplier tubes, mounting plate and signal processing card.
Figure 2C:
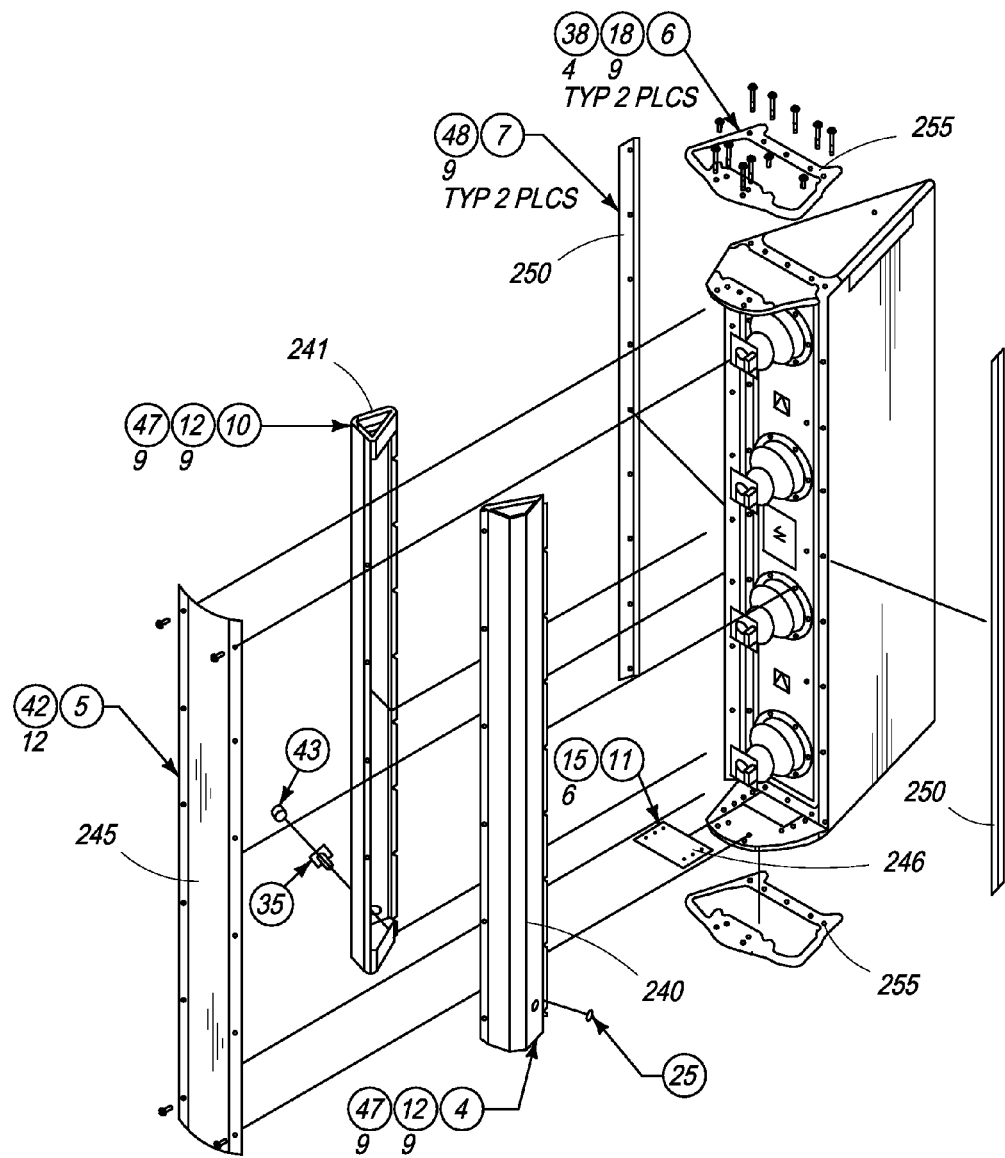
FIG. 2C shows an exploded view of the structures that cover the assembly of the photomultiplier tubes, mounting plate and signal processing card within the detector tower.
Figure 2D:
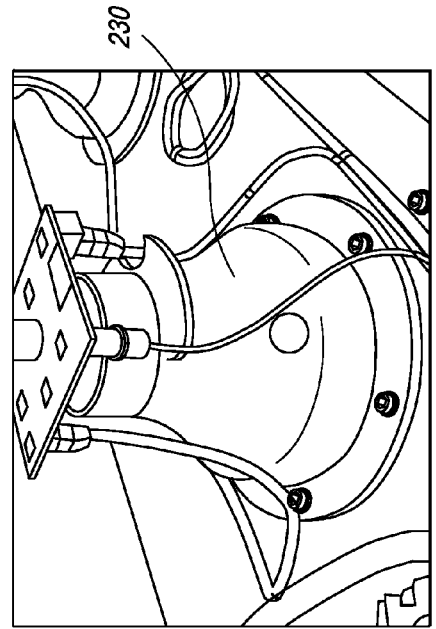
FIG. 2D shows a photomultiplier tube assembly in accordance with an embodiment of the present invention.
Figure 2E:
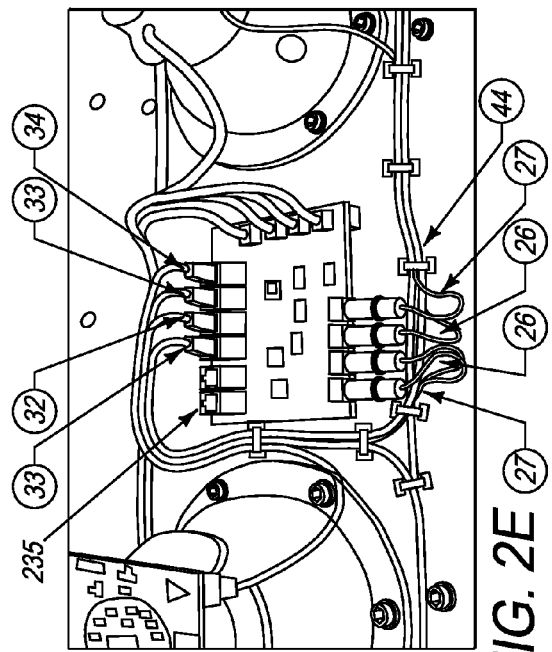
FIG. 2E shows a signal processing board in accordance with an embodiment of the present invention.

Referring now to exploded views of the detector towers in FIGS. 2B and 2C, simultaneously, the mounting plate 225 is shown as "broken-away" and separate from the four photomultiplier tube assemblies 230 that are mounted on the plate 225 when assembled. In accordance with an embodiment of the present invention, back-end electronics of the photomultiplier tubes 230 comprises a signal processing board 235 co-located on the mounting plate 225 in proximity to the photomultiplier tubes. FIG. 2D provides a more detailed view of the photomultiplier assembly 230 while FIG. 2E shows a detailed view of the signal processing board 235 that in this embodiment is a four-channel card corresponding to the four photomultiplier tubes.

Figure 2F:
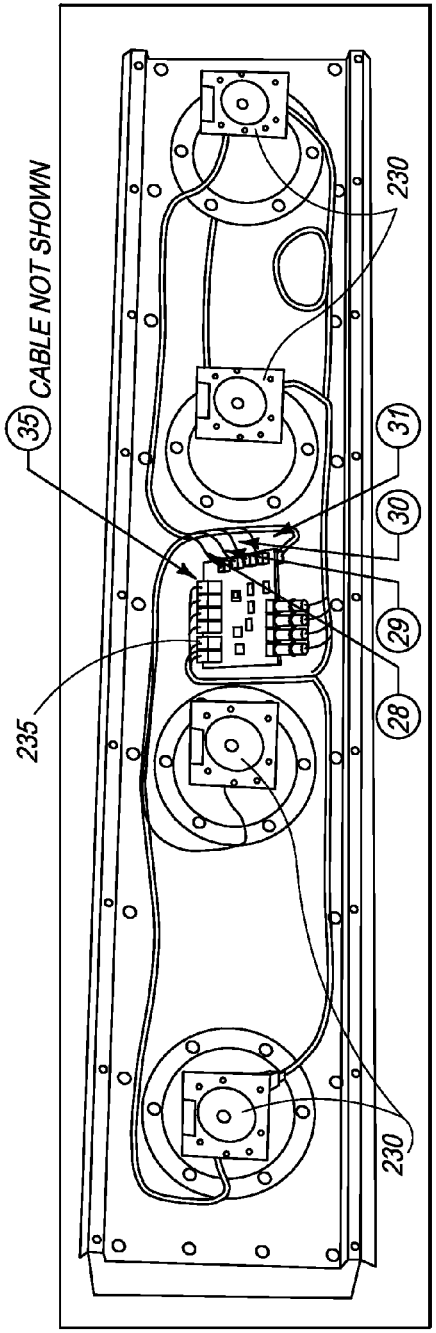
FIG. 2F shows the wiring connections of four photomultiplier tubes with the signal processing board.

At least one analog to digital conversion card and a power supply module is mounted on the signal processing board 235. The power supply module applies an operating voltage to the photomultiplier tubes while the analog to digital conversion card converts pulse current output from the photomultiplier tubes into digital signals for further processing. Conventionally, massive cables are employed to connect the photomultiplier tubes with a central analog-to-digital converter and power station located at a distance from the photomultiplier tubes. By having power supply as well as analog-to-digital converter closer to the photomultiplier tubes, smaller wires are needed thereby also reducing signal transient noise and improving the overall signal-to-noise ratio (SNR). Similarly, FIG. 2F shows wiring connections of the four photomultiplier tubes 230 with the signal processing board 235.

Referring again to FIGS. 2B and 2C, simultaneously, a seal 226 allows the assembly comprising mounting plate 225, photomultipliers 230 and signal processing board 235 to fit tightly into the corresponding tower premise 227. An interconnectable set of structures cover, both protect and allow easy access when needed to the photomultiplier tubes located on the mounting plate assembly. These set of structures comprise a corner cover 240 with a connector corner cover 241; a closure cover 245 with a corresponding connector 246; two trim side plates 250 and top and bottom handle frames 255.

Referring back to FIG. 1, in one embodiment, the inspection system 100 has modular components that can be disassembled for mobility and ease of transportation and reassembled again at the site of interest. Thus, the teardrop-shaped detector towers 110, 120 and the radiation source housing 165 with associated electronics and cables are manufactured as separate modules or cabinets that can be integrated quickly to form the system 100. The novel teardrop modular architecture enables a compact and light overall system 100.

FIG. 3A shows a disassembled view 300a of the screening system of the present invention such that its modular components, such as detector towers 310, 320 along with radiation source housing 365, are unassembled and packaged for ease of transportation. For example, the triangular cross-section of detector towers 310, 320 enables these to be packaged abutting each other in a way that requires minimal space for transportation. FIG. 3B shows an assembled view 300B of the screening system that has been constructed from the transportable package 300a of FIG. 3A. The modular components or cabinets of the screening system of the present invention are designed such that they have simple and intuitive points of connection, such as being able to be fastened to each other, via snap buttons, for quick assembly. In one embodiment, it takes less than 30 minutes to assemble/deploy the screening system from its transportable, packaged condition. In one embodiment, it takes approximately 15 to 30 minutes to assemble/deploy the screening system from its transportable, packaged condition. In one embodiment, the assembly/deployment time is dependent upon whether the unit must be heated or cooled to bring the unit to safe operating temperatures.

Persons of ordinary skill in the art should appreciate that the modular components design of the screening system of the present invention also facilitates ease of service access for repair and maintenance.

Figure 4:
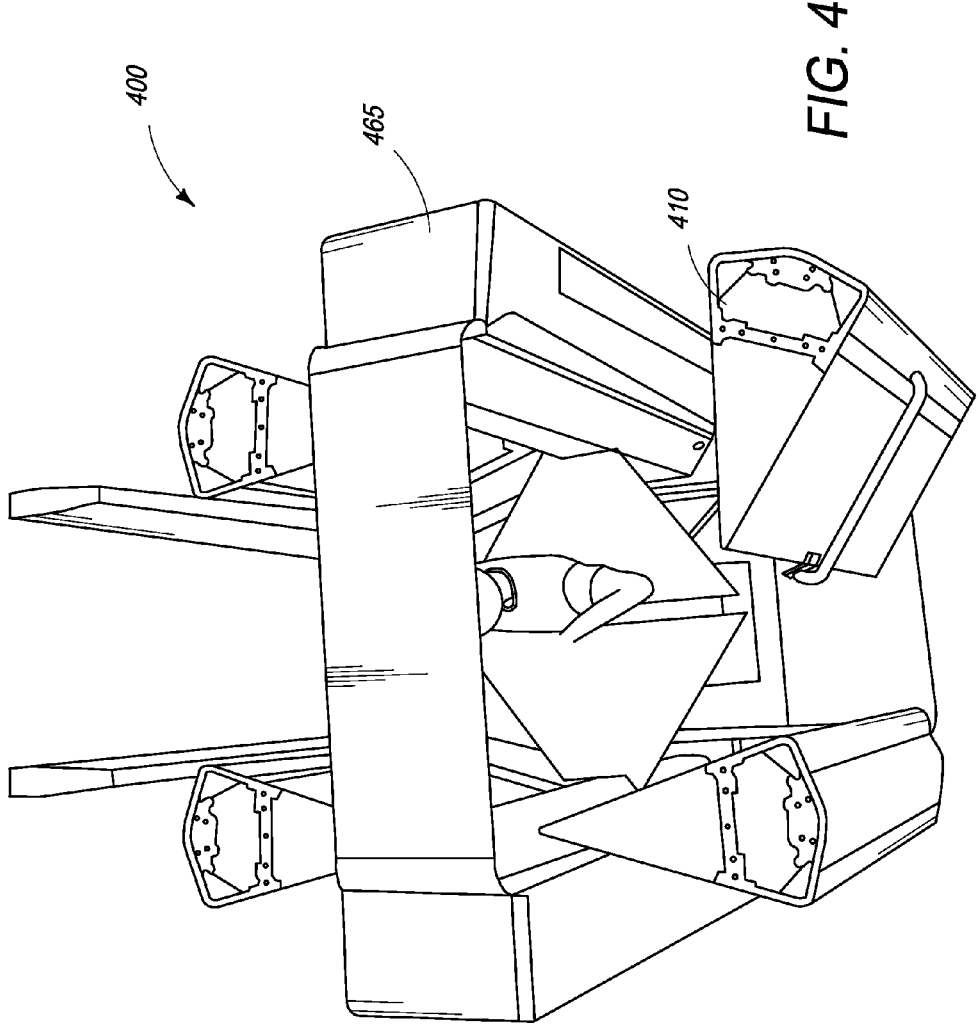
FIG. 4 illustrates a detector tower pulled apart from the radiation housing for ease of service access to the modular components of the screening system of the present invention.

For example, FIG. 4 shows an assembled/deployed view 400 of the screening system of the present invention with detector tower 410 being pulled away from the radiation housing 465 for service access to the housing 465 and/or for selective repair and maintenance of the tower 410.

Referring back to FIG. 1, during operation, as the subject 103 walks-by or stands in front of the detector towers 110, 120 a part of the pencil beam 102 of X-rays that strikes the subject 103 are back-scattered, as rays 105 due to Compton scattering and impinge on the first screen 147 at the front side area 141 of the detector towers. While a portion of the scattered X-rays are detected by the first screen 147, some portion of theses get transmitted through the first screen 147 without being detected and impinge on the second screen 148 (at side 142) in the interior of the detector towers. In one embodiment approximately 40% of the X-ray photons impinging the first screen 147 are detected by it while approximately 24% of the remaining X-ray photons are detected by the second screen 148. It should be noted that these percentages may change, depending upon the energy of the x-rays and the thickness of the scintillator screen.

The photomultiplier tubes 150 generate electronic signals in response to detected rays that are initially converted into light. The light emitted by scintillation at screens 147, 148 is bounced around the triangular enclosures/towers 110, 120 until fully captured with the photomultiplier tubes 150.

The electronic signals produced by the two detector towers 110, 120 are directed to a processor. The processor analyzes the received signals and generates an image on a display means. The intensity at each point in the displayed image corresponds to the relative intensity of the detected scattered X-rays as the beam is rastered across the subject. In one embodiment, X-ray source 160 communicates synchronization signals to the processor. The processor analyzes the detected signals and compares them to the synchronization signals to determine the display image. In one embodiment, the display means is a monitor and is employed to display graphical images signaled by the processor. Display means can be any display or monitor as commonly known in the art, including a cathode ray tube monitor, an LCD monitor or an LED monitor. In one embodiment, the digitized scatter image displayed by the display means preferably consists of 480 rows by 160 columns with 8 bits per pixel. Image processing techniques are described in greater detail below.

As described above, pencil beam 102 is rastered either horizontally or vertically across the subject, by employing a beam chopping mechanism by only allowing a minimal exit aperture for the x-ray beam to project. In one embodiment, the beam chopping mechanism is a chopper wheel having three slits positioned at 120 degrees apart and aligned with two parallel collimator slits such that each chopper slit will leave one of the parallel collimator slits while another is just entering the opposite parallel slit. This creates two parallel scanning beams that are interleaved in time and can be processed separately even with a single common detector array, circuitry and processing, all using a single source which conically illuminates the two parallel slits.

Figure 5A:
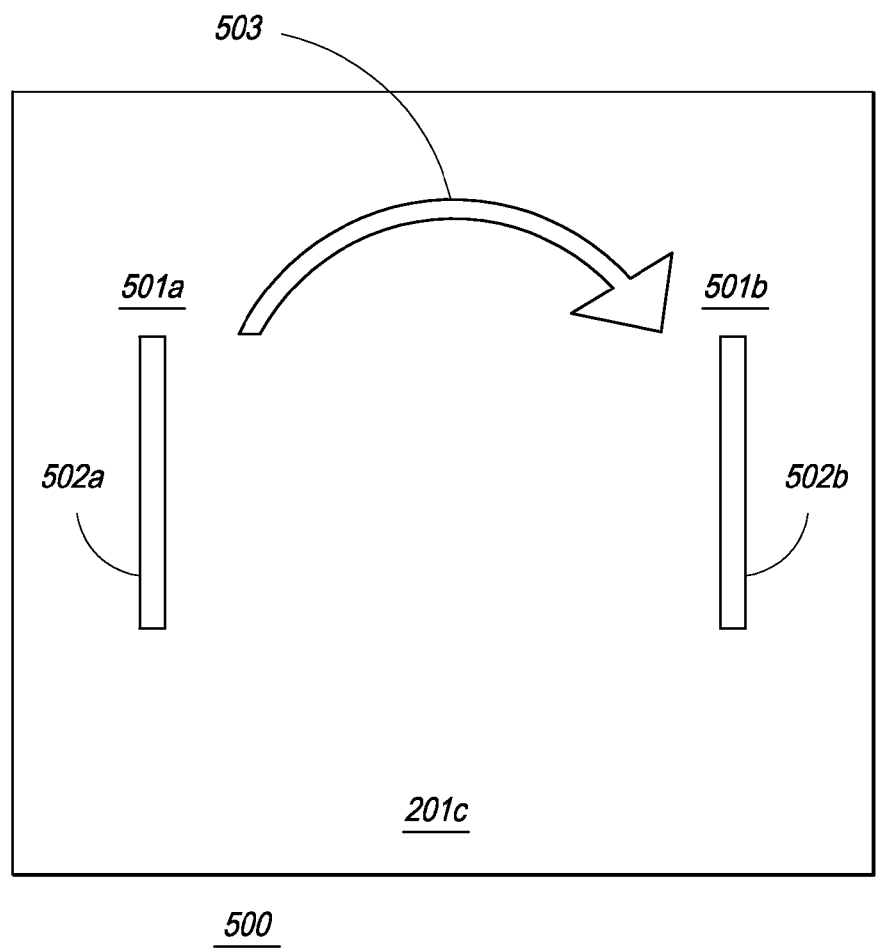
FIG. 5A illustrates a top view of an exemplary chopper wheel used in the screening system of the present invention.

FIG. 5A illustrates a top view of an exemplary chopper wheel 500 which can be used for obtaining a dual view (using two parallel, interleaved scanning beams) using a single source. The chopper wheel 500 has three slits, 501a, 501b and 501c, placed at an angular distance of 120 degrees from each other. There are also two parallel collimator slits 502a and 502b. Arrow 503 depicts the direction of motion of the chopper wheel, which in this embodiment is clockwise. This arrangement creates two "staggered" parallel scanning beams which, as mentioned earlier, are interleaved in time and can thus be processed separately using common detectors, circuitry and processing components.

Figure 5B:
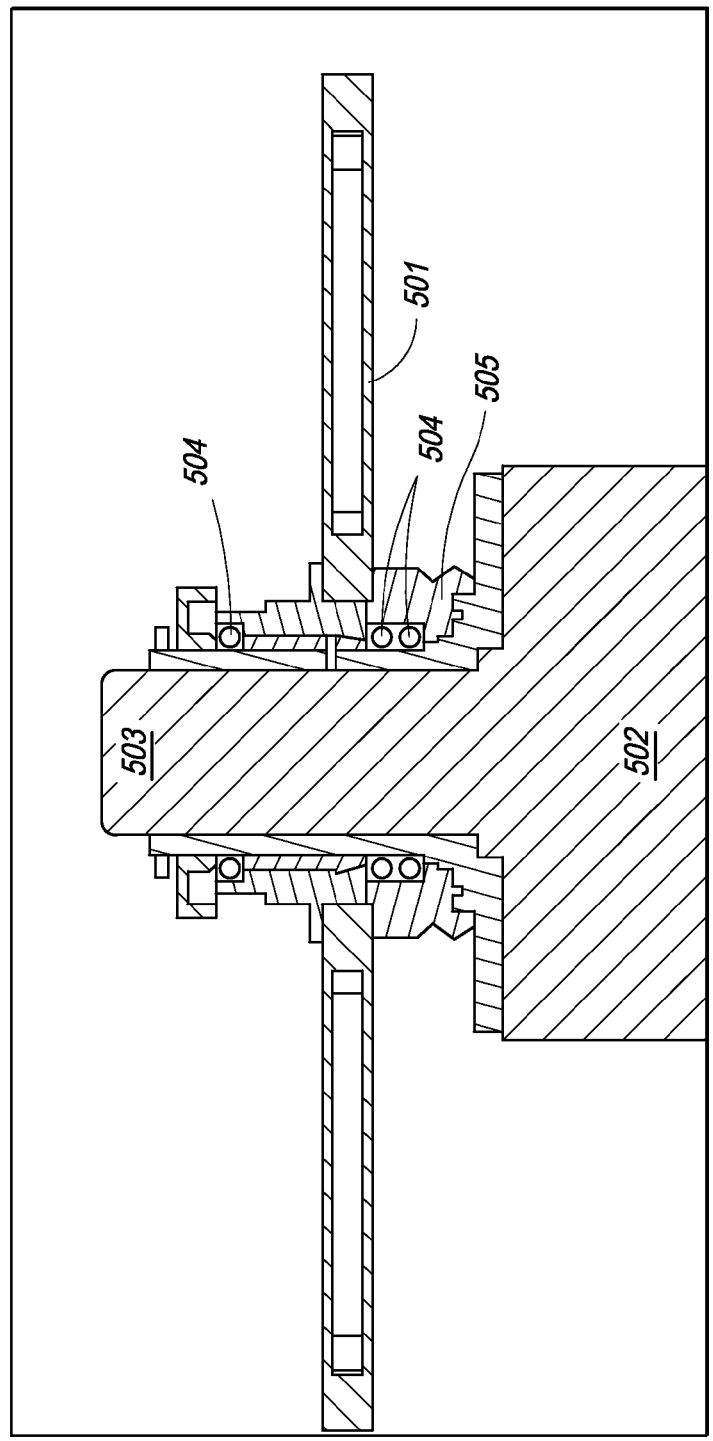
FIG. 5B illustrates an exemplary disk chopper assembly, with integrated electromagnetic motor and bearings.

In one embodiment, the disk chopper assembly is dynamically controlled for rotation using an electromagnetic motor drive. FIG. 5B illustrates an exemplary disk chopper assembly, with integrated electromagnetic motor and bearings. Referring to FIG. 5B, the disk chopper 501 is coupled to the radiation source 502, which, in one embodiment, comprises an X-ray tube. The electromagnetic motor 503 is integrated with the X-ray tube 502 and the chopper 501. The motor assembly further comprises three compression bearings 504, and a V-groove 505 for belt drive backup.

Figure 5C:
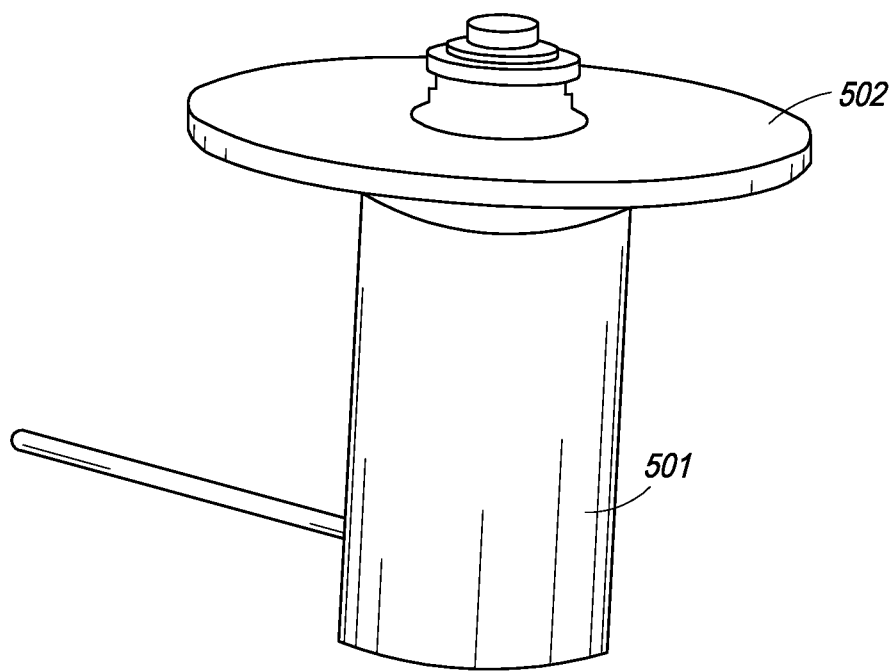
FIG. 5C illustrates an X-ray source coupled to a disk chopper, according to one embodiment of the present invention.

In one embodiment, the radiation source comprises an X-ray tube, which is preferably controlled by the X-ray controller. Two cooling fans are provided to dissipate the heat generated around the X-ray tube. The X-ray source is coupled to a disk chopper. Chopper motor is provided to effectuate rotation of the chopper wheel. The chopper motor is in turn controlled by a controller unit, which is also equipped with a suitable power supply. AC distribution and DC power supplies for the whole detection unit are placed at the bottom of the enclosure. FIG. 5C illustrates the X-ray tube (source) 501 coupled to the disk chopper 502, minus the motor assembly.

In one embodiment, the X-ray inspection system further comprises a reference detector that compensates and monitors each emitted beam and further functions as a radiation monitor for monitoring emitted radiation within the inspection region. The reference detector is, in one embodiment, positioned within the beam path before the beam chopping apparatus, such as the beam chopper disk. The reference detector is may also be positioned after the beam chopping apparatus, such as the beam chopper disk, at the beginning of the formed scanned line. In such a case, the radiation detector may acceptably block the first 2 degrees of the beam.

Figure 6A:
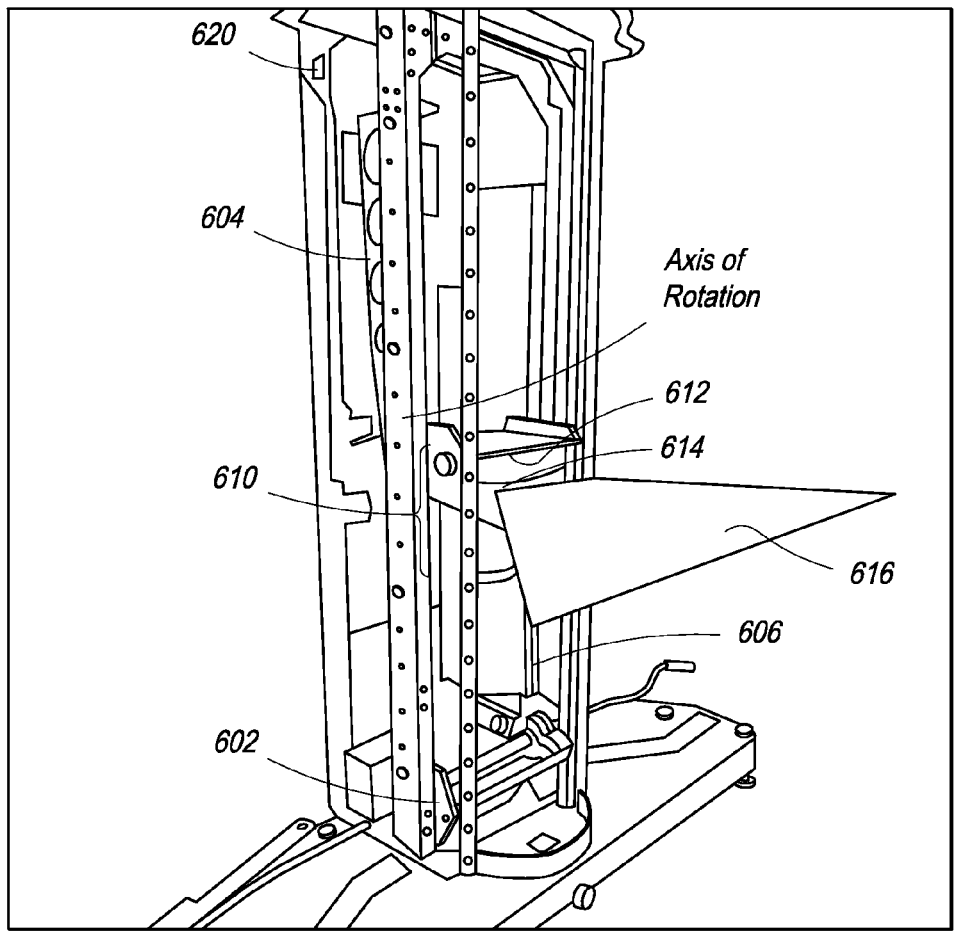
FIG. 6A illustrates an X-ray source being used in conjunction with a chopper wheel in an exemplary threat detection system, further showing a tilt "CAM" mechanism coupled to a source.

FIG. 6A illustrates an X-ray source being used in conjunction with a chopper wheel, as described in FIGS. 5A, 5B, and 5C, in an exemplary threat detection system. The source and chopper wheel are couple to a tilt "CAM" mechanism such that it enables substantially equal spacing between scan lines throughout the vertical motion of the x-ray beam. Referring to FIG. 6A, the module comprises a tilt CAM mechanism 602 coupled with an x-ray source assembly 610 all housed on frame 620. The tilt CAM mechanism 602 further comprises CAM guide 604. In addition, also housed on frame 620 is a motor for driving CAM mechanism and the belts used to lift the source. In one embodiment, a handle is attached to the source assembly 610 for enabling fitting in and removing the source assembly from the metal CAM guide frame 604. In various embodiments, all parts of the source assembly are securely attached by using predefined sizes of nuts, screws and clamps. In addition, lift belt 606 is provided to further enable lifting and counterbalancing of the source.

Figure 6B:
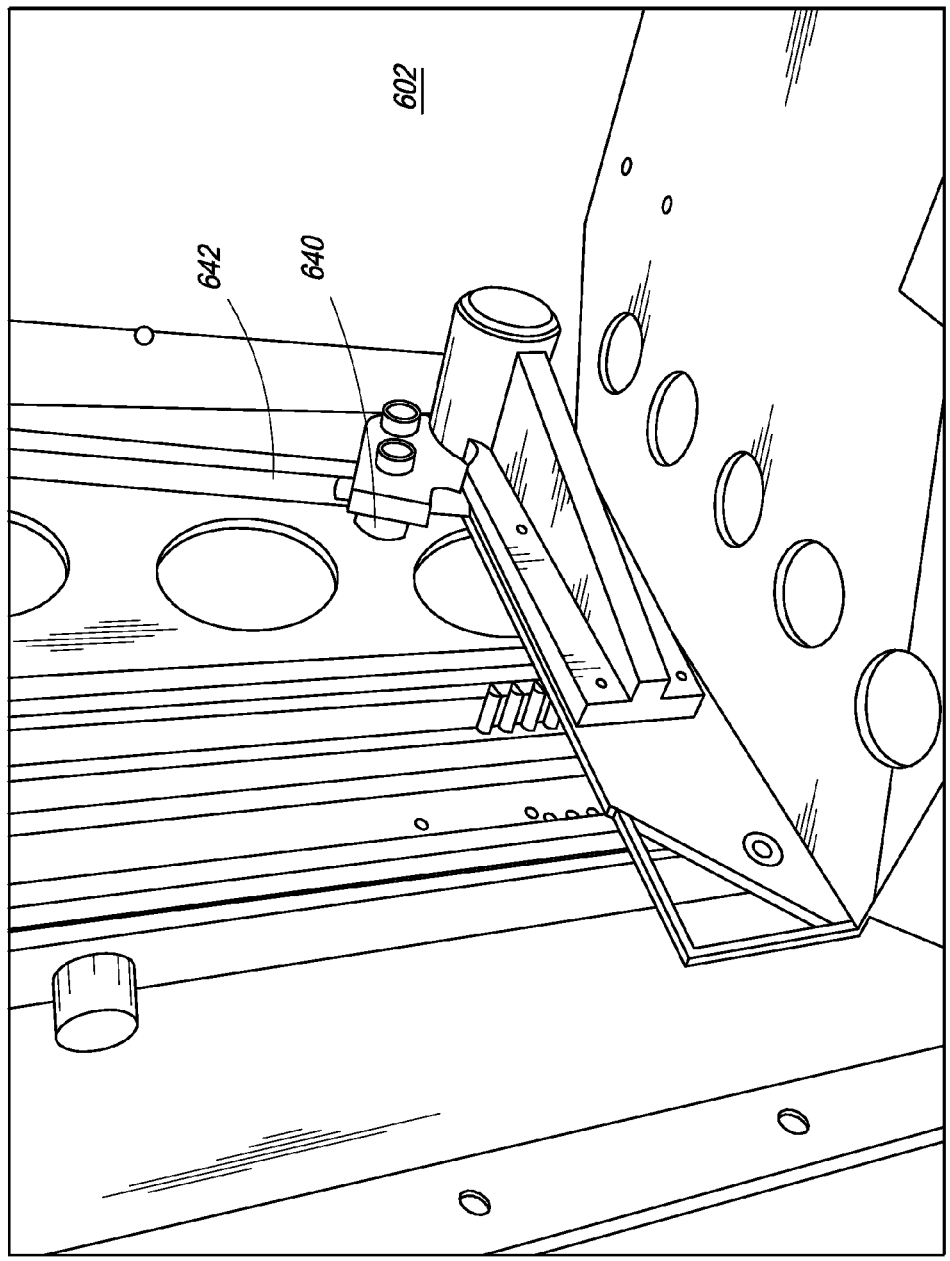
FIG. 6B shows a diagram of the metal frame title CAM mechanism 600 in an expanded view, further showing the drive wheel up against a CAM arm, such that it enables vertical motion of the source.

FIG. 6B shows a diagram of the tilt CAM mechanism 602 in an expanded view, further showing drive wheel 640 abutted up against CAM arm 642 such that it enables vertical motion of the source.

In another embodiment, a counterweight is employed to counterbalance the source and reduce stress on the lifting motor. In another embodiment, two lift belts may be employed to balance the source, eliminating the counterbalance and resulting in a much lighter source. In another embodiment, a gear reducer (15:1 reduction) and higher torque motor may be employed to eliminate the use of a counterbalance, as the source now seems 15 times lighter to the motor. However, the motor, in this case, would have to turn 15 times faster to achieve the same radiation pattern.

Figure 6C:
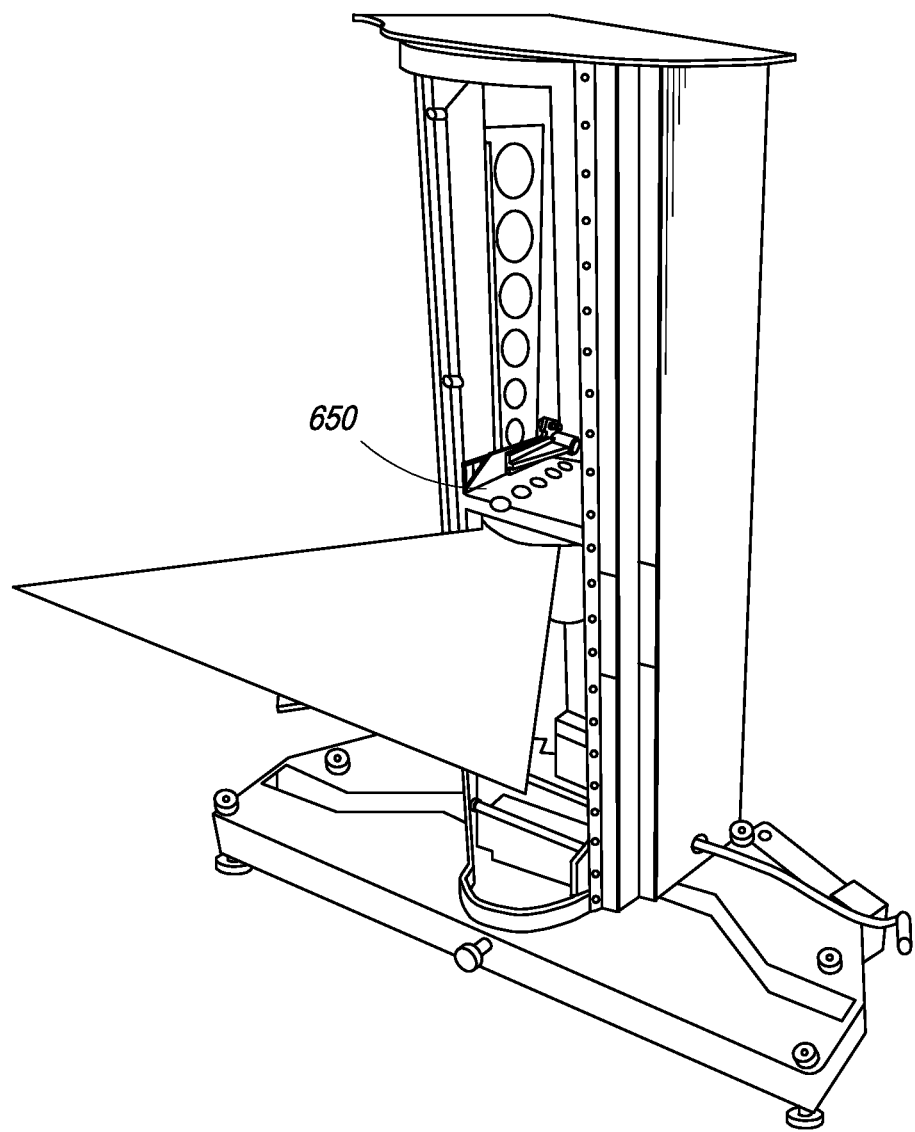
FIG. 6C illustrates another view of the module illustrated in FIG. 6A, further showing a rotating platform to rotate the source and corresponding power supply.

Referring back to FIG. 6A, the source assembly 610 comprises an X-ray source 612 and a disk wheel chopping mechanism 614 made of a suitable material such as metal or plastic for guiding the X-rays 616 generated by the X-ray source in a desired direction. In one embodiment, source assembly 610 also comprises a high voltage power supply enabling the operation of the source assembly. In an embodiment, the X-ray source 612, along with beam chopping mechanism 614, generates a narrow pencil beam of X-rays which are directed towards a subject under inspection through source rotation or beam traversal to create a scan line. In one embodiment, the disk wheel chopping mechanism 614 is optionally coupled with a cooling plate, which dissipates heat generated by the rotating chopper wheel. FIG. 6C illustrates another view of the module illustrated in FIG. 6A, further showing a rotating platform 650 to rotate the source and corresponding power supply to enhance the resultant field of view, as described in detail below with respect to FIG. 13.

It should be understood by persons having ordinary skill in the art that radiation sources are typically very heavy. In order to accommodate for the weight of the X-ray source, a chopper wheel configuration, as employed above, has to be rather large, and thus contributes to the overall weight of the system. Therefore, in another embodiment, the screening system of the present invention is equipped with a spin-roll chopper that is designed to present a helical profile aperture shutter for X-ray beam scanners and that is lightweight and easy to deploy. In addition, the use of the spin-roll chopper obviates the need for source rotation, rather the beam traverses from −45 to +45 degrees.

In one embodiment, the spin-roll chopper allows for variability in both velocity and beam spot size by modifying the physical characteristics or geometry of the beam chopper apparatus. In addition, the spin-roll chopper provides a vertically moving beam spot with constant size and velocity to allow for equal illumination of the target and creates a wider field of view during operation.

Figure 7A:
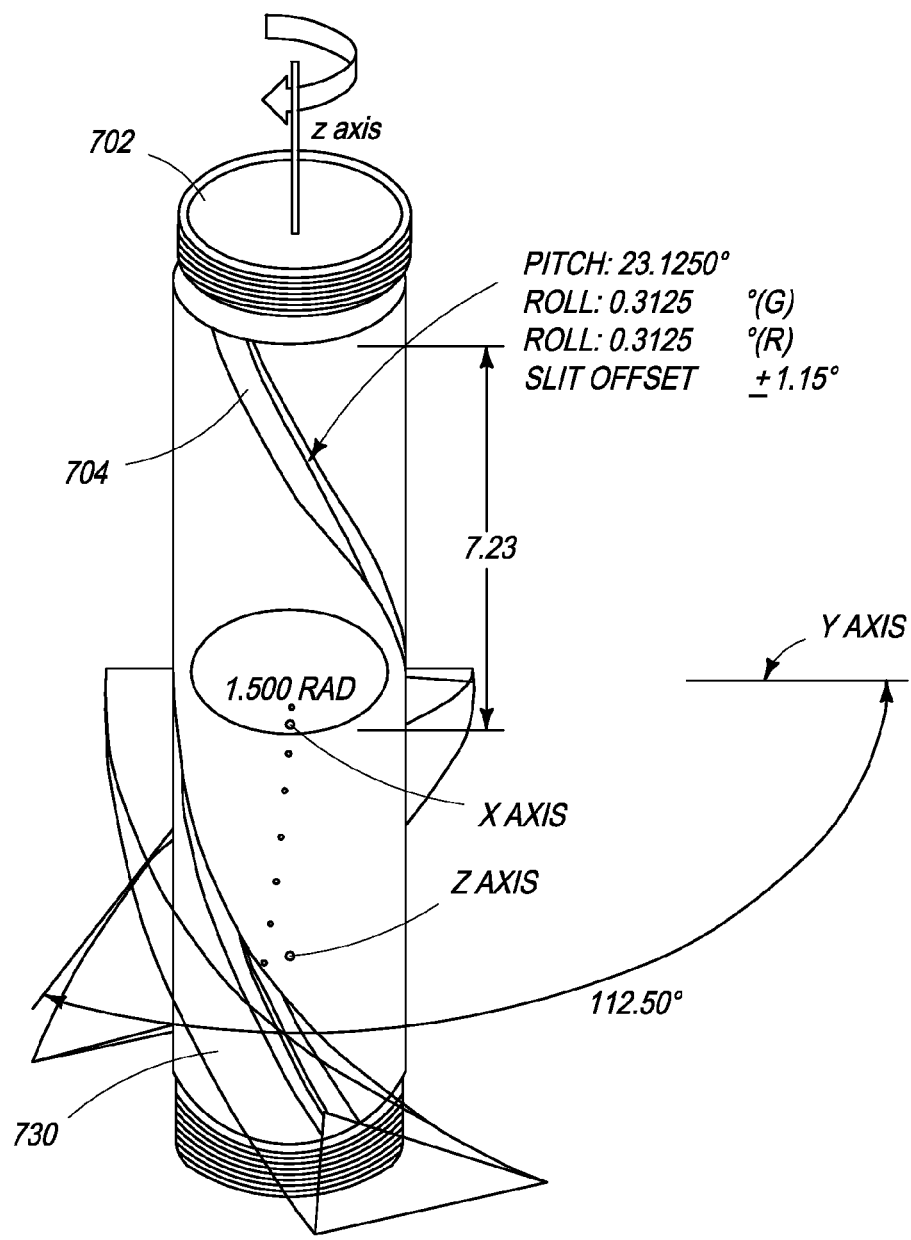
FIG. 7A is a mechanical illustration of an exemplary design of one embodiment of an exemplary beam forming apparatus.

FIG. 7A illustrates an exemplary design for one embodiment of the spin-roll chopper, as used in various embodiments of the present invention. Beam chopper 702 is, in one embodiment, fabricated in the form of a hollow cylinder having helical chopper slits 704. The cylindrical shape enables the beam chopper 702 to rotate about the Z-axis and along with the helical apertures 704, create a spin-roll motion.

Thus, an X-ray beam scanner employing the spin-roll chopper of the present invention effectuates beam chopping by rotating the hollow cylinder 702 machined with at least two helical slits 704, which enables X-ray beam scanning with both constant and variable linear scan beam velocity and scan beam spot size. The spin-roll chopper enables both constant and variable linear scan beam velocity by manipulating the geometry of the helical apertures. In one embodiment, the velocity is varied or kept constant by manipulating the pitch and roll of the helical apertures along the length of the spin-roll chopper. Thus, it is possible to have a constant speed or to slow the scan down towards areas where more resolution is desired.

The spin-roll chopper also enables variable and constant beam spot size by manipulating the geometry of the helical apertures, thus varying the resultant beam power. In one embodiment, it is possible to manipulate the actual width of the aperture to alter the beam spot size. In one embodiment, the width of the helical aperture varies along the length of the spin-roll chopper cylinder to compensate for the varying distance of the aperture from the center of the source and allow for uniform beam spot projection along the scan line. Thus, in one embodiment, the farther the aperture is away from the source, the narrower the width of the helical aperture to create a smaller beam spot size. In one embodiment, the closer the aperture is to the source, the wider the helical aperture to create a larger beam spot size.

When employed in a body scanning system, it is possible to vary the pitch and roll and width of the helical apertures such that more beam scanning power is directed towards areas of the body (hair, feet, etc) that require more detail and resolution and less power is directed towards areas of the body (midsection, etc.) that are more sensitive to radiation.

Helical slits 704 also ensure that the projection of the X-ray beam is not limited by the dual collimation of the two slits. As described in greater detail below, dual collimation refers to the concept whereby the X-ray beam will pass through two helical slits at any given point in time. The resultant X-ray beam trajectory 730 is also shown in FIG. 7A and described in greater detail with respect to FIG. 7C below.

In an embodiment of the present invention a plurality of viewing angles ranging from sixty degrees to ninety degrees can be obtained through the helical slits in the spin-roll chopper. In one embodiment, the scan angle is a function of the distance between the spin-roll chopper and both the source and the target. In addition, the overall height and diameter of the spin-roll chopper affects the viewing angle. The closer the spin-roll is placed to the source, the smaller the spin-roll chopper will need to be and similarly, the farther the spin-roll chopper is placed from the source, the larger the spin-roll chopper would need to be.

Figure 7B:
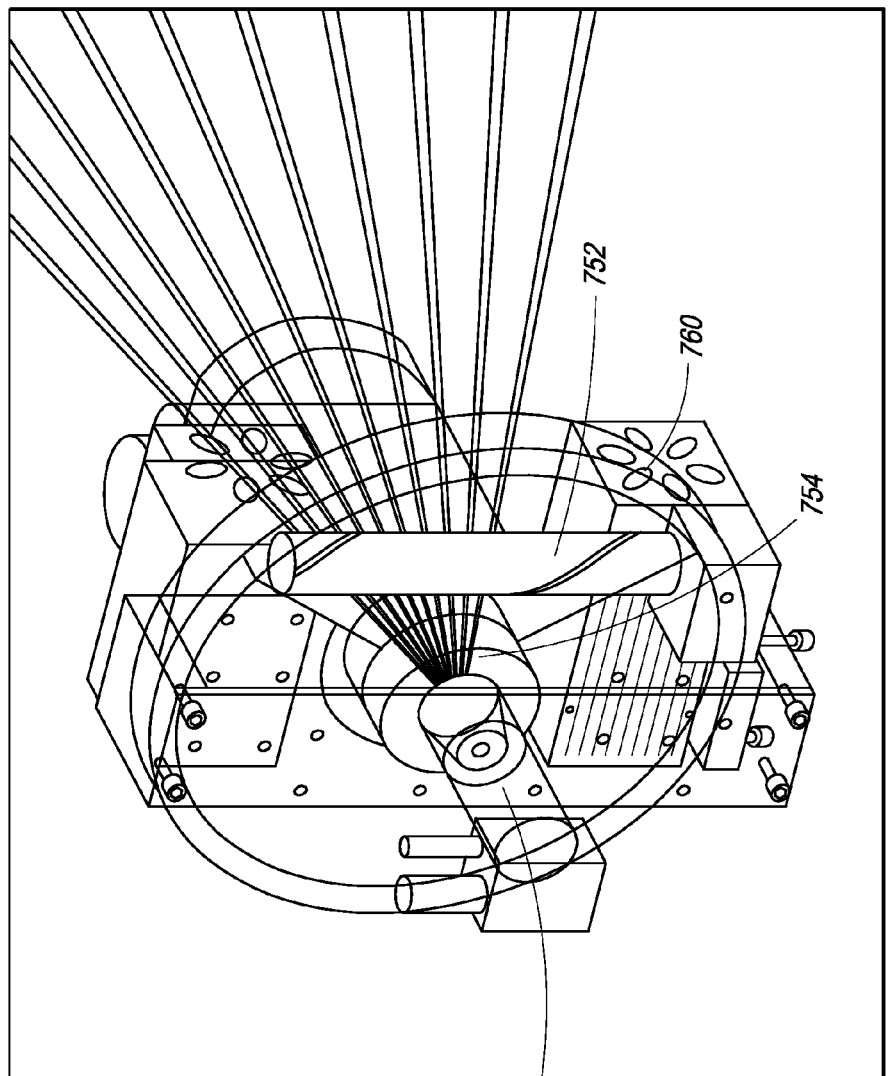
FIG. 7B illustrates an exemplary beam forming apparatus with an X-ray source.

FIG. 7B illustrates a beam chopping mechanism using the spin-roll chopper described with respect to FIG. 7A. Referring to FIG. 7B, the cylindrical spin-roll chopper 752 is placed in front of a radiation source 754, which, in one embodiment, comprises an X-ray tube. In one embodiment, rotation of the chopper 752 is facilitated by including a suitable motor 758, such as an electromagnetic motor. In another embodiment, as described in greater detail below, magnetic bearings are employed to facilitate rotational movement of the spin-roll chopper of the present invention. The speed or RPM of rotation of the spin-roll chopper system is dynamically controlled to optimize the scan velocity. In one embodiment, the spin-roll chopper system is capable of achieving speeds up to 80K RPM.

In one embodiment, a radiation shield is provided on radiation source 754 such that only a fan beam of radiation is produced from the source. The fan beam of radiation emits X-rays and then passes through the spin-roll chopper, which acts as an active shutter. Thus, there is only a small opening when the spin-roll chopper, and therefore helical apertures are rotating, which provides the moving flying spot beam.

FIG. 7B also shows a disk chopper wheel 760 superimposed upon the source along with the spin-roll chopper. It can be seen from FIG. 7B that chopper wheel 760 is substantially larger than spin-roll chopper 752.

Figure 7C:
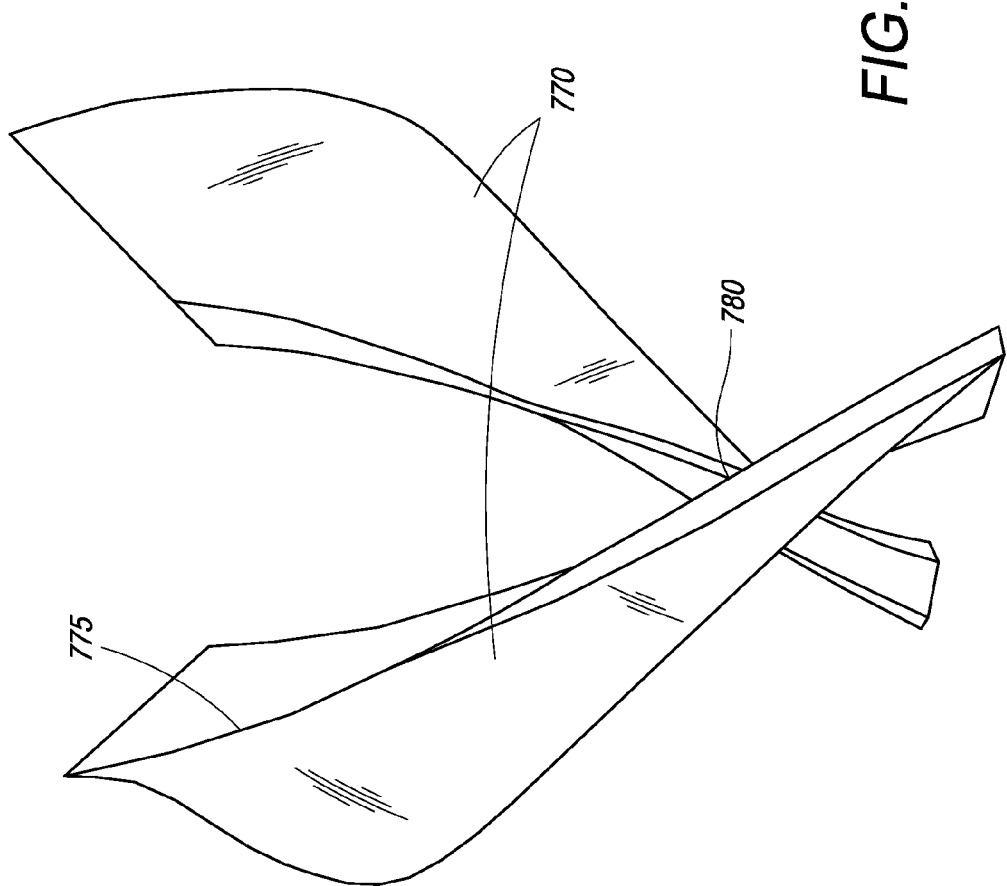
FIG. 7C is a mathematical expression of the trajectory of the beam using the spin-roll chopper of the present invention with a single source, in accordance with one embodiment.

In accordance with an embodiment of the present invention, at certain distances from the center of the beam, the helical slit (of the spin roll chopper) is kept wider than others. FIG. 7C shows a mathematical expression of the trajectory 770 of the beam using a single source, in accordance with one embodiment. In order to get the dimensions of the helical cuts in the spin-roll cylinder, one dimension of this trajectory was removed. More specifically, the slit is narrower at the top 775 because there is a greater distance for the beam to travel. Note that when an X-ray beam travels through any opening, the beam is collimated. The farther the beam travels, the wider the resultant "spot" (fan beam) is at the end of the beam. By making the slit narrower at the top 775, this greater distance and beam widening is accounted for. In addition, the slit is made wider where the distance to the object is shorter, such as at point 780. Also, persons of ordinary skill in the art should appreciate that by controlling the size of the slit one can control the density of the beam that is projected straight through.

U.S. Provisional Patent Application No. 61/313,772 entitled "Walk-Through People Screening System" and filed on Mar. 14, 2010, and its corresponding children applications are incorporated herein by reference in their entirety.

The system of the present invention is designed such that the distance of the beam chopping mechanism from the target is directly correlated with a minimum scan height. This allows for longer distance from source to the target, thereby extending the depth of field with respect to dose rate to the target. Therefore, for a given depth of imaging, a smaller radiation dose is required with the system of the present invention as compared to other systems known in the art.

In an embodiment, the screening system is based on the X-ray backscatter method. In X-ray backscatter systems for detecting concealed objects, a pencil beam of X-rays traverses over the surface of the body of a subject being examined. X-rays that are scattered or reflected from the subject's body are detected by a detector such as, for example, a scintillator and photomultiplier tube combination. The resultant signal produced by the X-ray detector is then used to produce a body image, such as a silhouette, of the subject and any concealed objects carried by the subject. The design of the X-ray backscatter imaging system of the present invention is optimized for near-real time imaging of people or objects with an interrogating radiation beam. The system is also capable of automatically detecting threats by processing detection algorithms on the image data in near real-time.

In a first embodiment, the x-ray screening system of the present invention is implemented as a stationary screening system wherein a person being inspected is required to stop at a predetermined position and assume a pose enabling scanning.

In a second embodiment, the X-ray screening system of the present invention is implemented as a walk-through system wherein a person being inspected is required to walk through the system, while being scanned.

In order to obtain 2-D images of scattered radiation, detector systems make use of a dual-axis scanning beam.

Embodiment 1

Figure 8A:
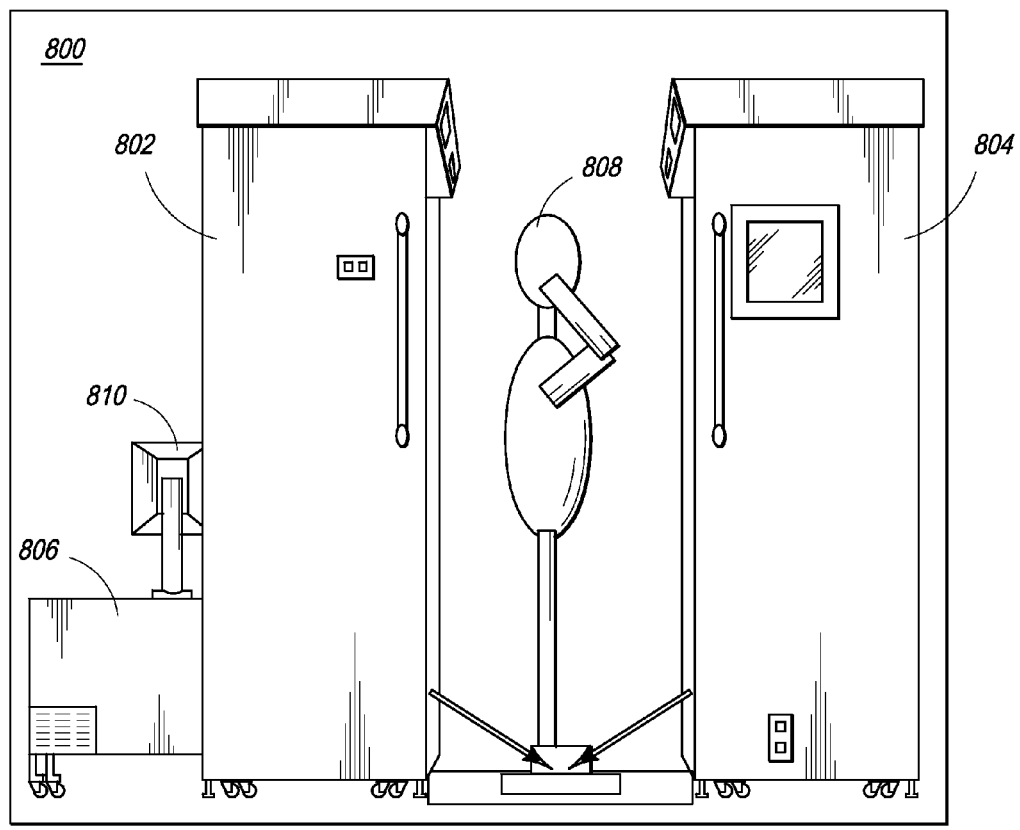
FIG. 8A illustrates one embodiment of an implementation of the screening system of the present invention, in which the subject under inspection assumes a stationary posture.

FIG. 8A illustrates a first embodiment of an implementation of the screening system of the present invention, in which the subject under inspection assumes a stationary posture. Thus, in an embodiment, the X-ray screening system of the present invention is implemented as a stationary screening system. FIG. 8A illustrates an exemplary design of the stationary pose implementation of the screening system of the present invention. The screening system 800 comprises a first scanning side 802, a second scanning side 804 and an operator station 806. A radiographic image of a person 808 being scanned is displayed on a screen 810 provided at the operator station 806.

Each scanning side comprises at least one radiation source and a plurality of detectors (not shown).

In one embodiment, the screening system of the present invention optionally includes a shoe scanner. Thus, in one embodiment, a shoe scanner is incorporated into the screening system of the present invention. Various shoe scanners may be used in conjunction with the screening system of the present invention.

U.S. patent application Ser. No. 12/948,738 entitled "X-Ray Based System and Methods for Inspecting a Person's Shoes for Aviation Security Threats" and assigned to the applicant of the present invention is herein incorporated by reference in its entirety.

In one embodiment, the two scanning sides 102 and 104 are connected at the top portion by a flat or arched ceiling forming an archway.

Figure 8B:
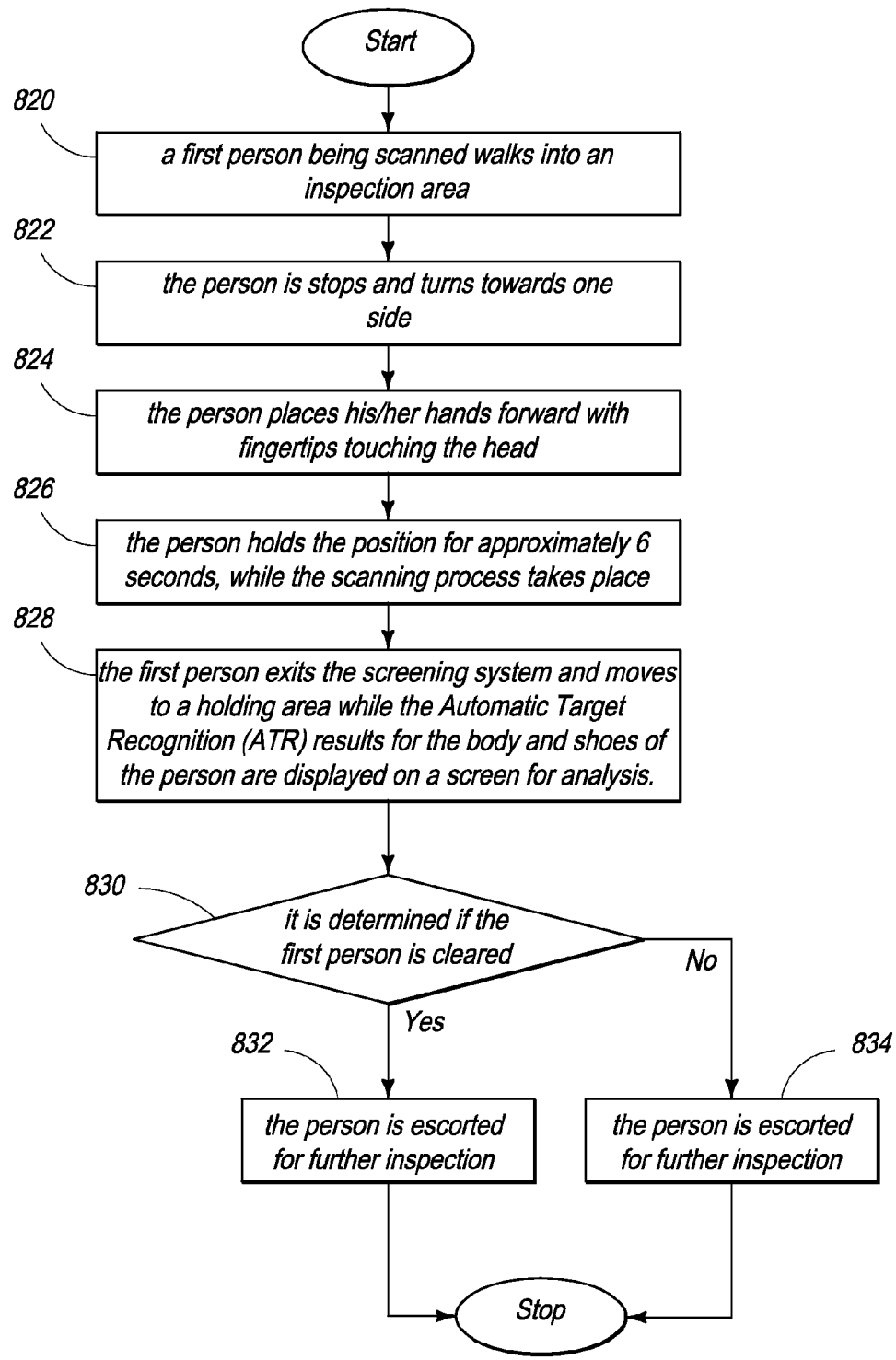
FIG. 8B is a flowchart illustrating the method of using the stationary posture implementation of the screening system of the present invention, shown in FIG. 8A.

FIG. 8B is a flowchart illustrating the method of using the stationary posture implementation of the screening system of the present invention, shown in FIG. 8A. Referring to both FIGS. 8A and 8B, at step 801 a first person being scanned walks into an inspection area defined by the two scanning modules 802 and 804, described with respect to FIG. 8A.

Referring back to FIG. 8B, at step 822 the person stops and turns towards one side. At step 824, the person places his/her hands forward with fingertips touching the head. The position of the person being scanned at step 824 is illustrated as 808 is FIG. 8A.

At step 826, the person holds the position for approximately 6 seconds, while the scanning process takes place.

At step 828, the first person exits the screening system 800 and moves to a holding area while the Automatic Target Recognition (ATR) results for the body and optionally, shoes of the person are displayed on a screen for analysis. Optionally at step 828, a next person to be scanned enters the inspection area defined by the two scanning modules 802 and 804.

At step 830 it is determined if the first person is cleared, i.e. if the scanned image of the first person has not revealed a threatening object. If the first person is cleared, he/she exits the holding area at step 832. If the first person is not cleared, he/she is escorted for further inspection at step 834.

In an optional embodiment, the person being scanned is provided instructions for scanning such as instructions to enter, turn to a side, lift hands etc. via a laser projection system. The laser projection system, in an embodiment, is embedded in a ceiling of the screening system 800 and displays instructions on either side 802 or 804 during the scanning process. In an embodiment, the laser projection system is designed to display instructions, status information, advertising, or any other data on the wall of scanning modules 802, 804 such that the displayed information is visible to a person being scanned during the scanning process.

In another embodiment, video analytics are used in the screening system 800 to evaluate a pose of a person being scanned prior to and during scan. The video analytics can implement various forms of optical detection, including infrared and visible light, to determine a) the shape of the individual's pose, b) compare the shape of the individual's pose to a plurality of acceptable shapes stored in a library, c) generate a signal based upon said comparison if the shape of the individual's pose fails to comply with at least one of the plurality of acceptable shapes, within a margin of error, and d) provide an alarm, instruction, or other indicator to prompt a person to modify his or her pose in order to form an acceptable shape.

Embodiment 2

In another embodiment, the X-ray screening system of the present invention is implemented as a walk-through system wherein a person being inspected is required to walk through the system. In another embodiment of the present invention, and as shown in greater detail in FIG. 9A, a single axis scanning beam through which a target will walk is employed. The walking motion of the target provides the second axis of motion. Thus, a fixed vertical scan beam constitutes one axis of motion and the intended subject provides the second axis of motion by walking or being conveyed through the vertical scanning beam. The beam can be oriented for vertical motion to allow a smaller opening and optimum detector positioning, as described above.

Referring back to FIG. 1, at any one given instant where the subject under inspection 103 or target moves through the vertically moving pencil X-ray beam 102, the precise location of the beam is known via the motor that controls the chopper wheel (described in greater detail below). At each instant, the detector arrangement 106 provides the measured response of backscattered x-rays, the strength of which is represented in the resultant image. Because the system knows exactly where the pencil beam is located at every instant that the backscattered rays are detected, the image can be "stitched" together, to form the comprehensive image of the target.

In one embodiment, a fixed vertical scan beam constitutes one axis of motion and the intended subject provides the second axis of motion by walking or being conveyed through the vertical scanning beam. This configuration is advantageous because the single axis beam requires a very small rectangular opening at the detector panel when compared with current backscatter detection systems utilizing a dual-axis scanning beam, where the mechanical assembly requires a significant opening between the detectors to allow the scanning beam to exit. A significant opening is required because for a dual-axis scanning beam system when the target is stationary (where a spinning chopper wheel provides one axis of motion and the vertical motion of this spinning chopper wheel provides the second axis of motion) the pencil beam of x-rays is projected in the horizontal direction. Thus, to cover a target the size of a person, the opening must be wider to allow the beam to cover entire person. In addition, a conventional large sized opening allows a large portion of backscatter radiation to escape undetected.

The single axis scanning system of the present invention incorporates a small rectangular opening 172 between detector regions 110 and 120 for the X-rays to emanate therefrom. Further, the small opening 172 makes it possible to position additional and/or larger detector panels in the direct backscatter path, thereby enhancing image quality.

Figure 9A:
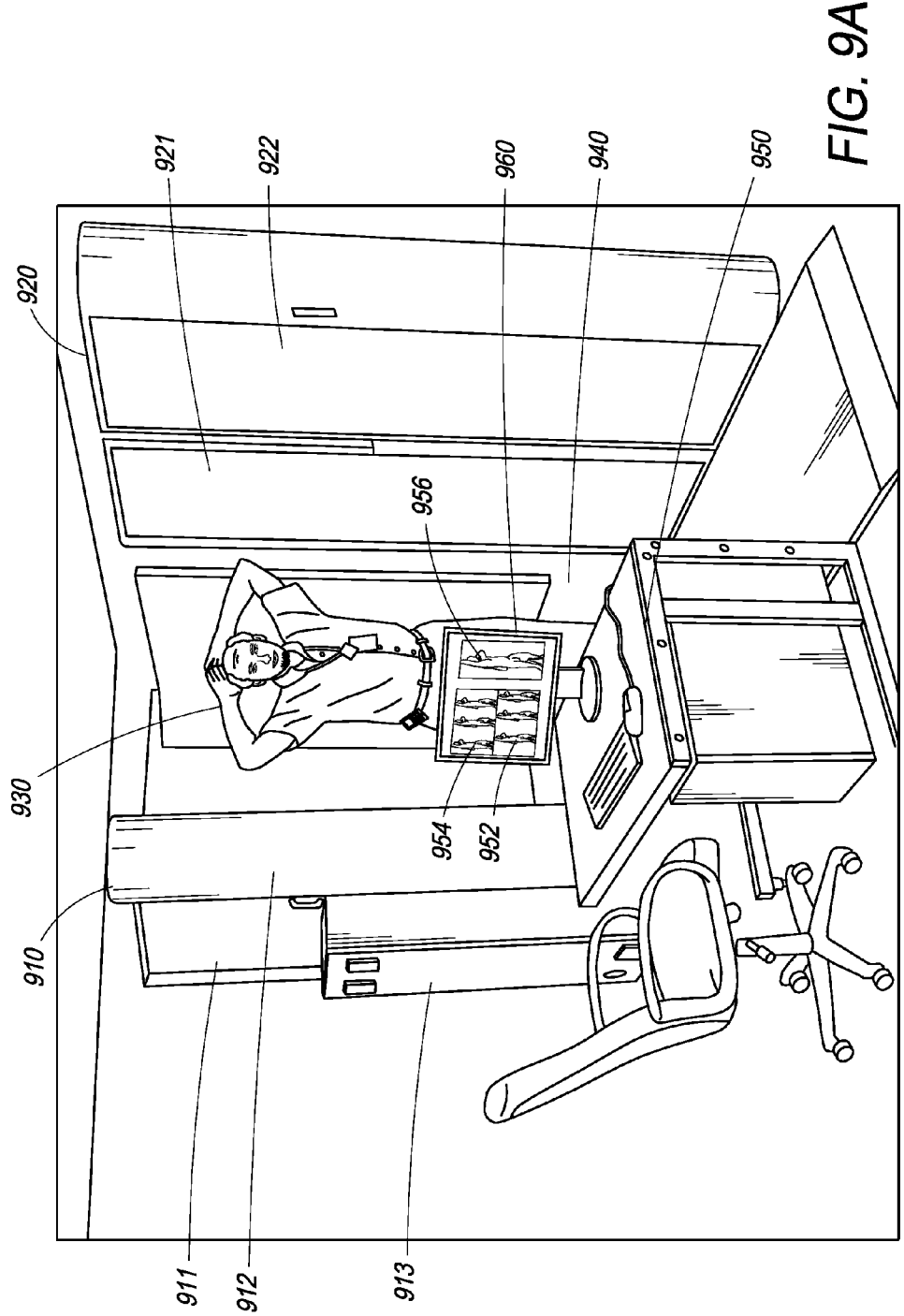
FIG. 9A illustrates another embodiment of the screening system of the present invention, in use, in which the subject under inspection walk through the system.

FIG. 9A illustrates one embodiment of the screening system of the present invention, in use, in which the subject under inspection walk through the system. Referring to FIG. 9A, first scanning side 910 and second scanning side 920 are used to create an inspection area through which the individual to be scanned walks. The first scanning side 910 comprises two detector panel towers 911 and 912. In one embodiment, X-ray enclosure 913 is also located proximate to first scanning side 910. Second scanning side 920 is positioned across the walkway from first scanning side 910, thus forming inspection area or volume 940. Second scanning side 920 comprises two detector panel towers 921 and 922. A second X-ray enclosure is located proximate to the second scanning side 920.

Operator's screen 960 also separately presents front and rear views 952 and 954, respectively, in addition to overall picture 956. Further, in this kind of walk-through arrangement, several persons can be rapidly screened by simply asking them to walk through the inspection area in a queue. In the exemplary application, the operator's screen 960 also shows queued front and rear images, 952 and 954, from three persons.

Figure 9B:
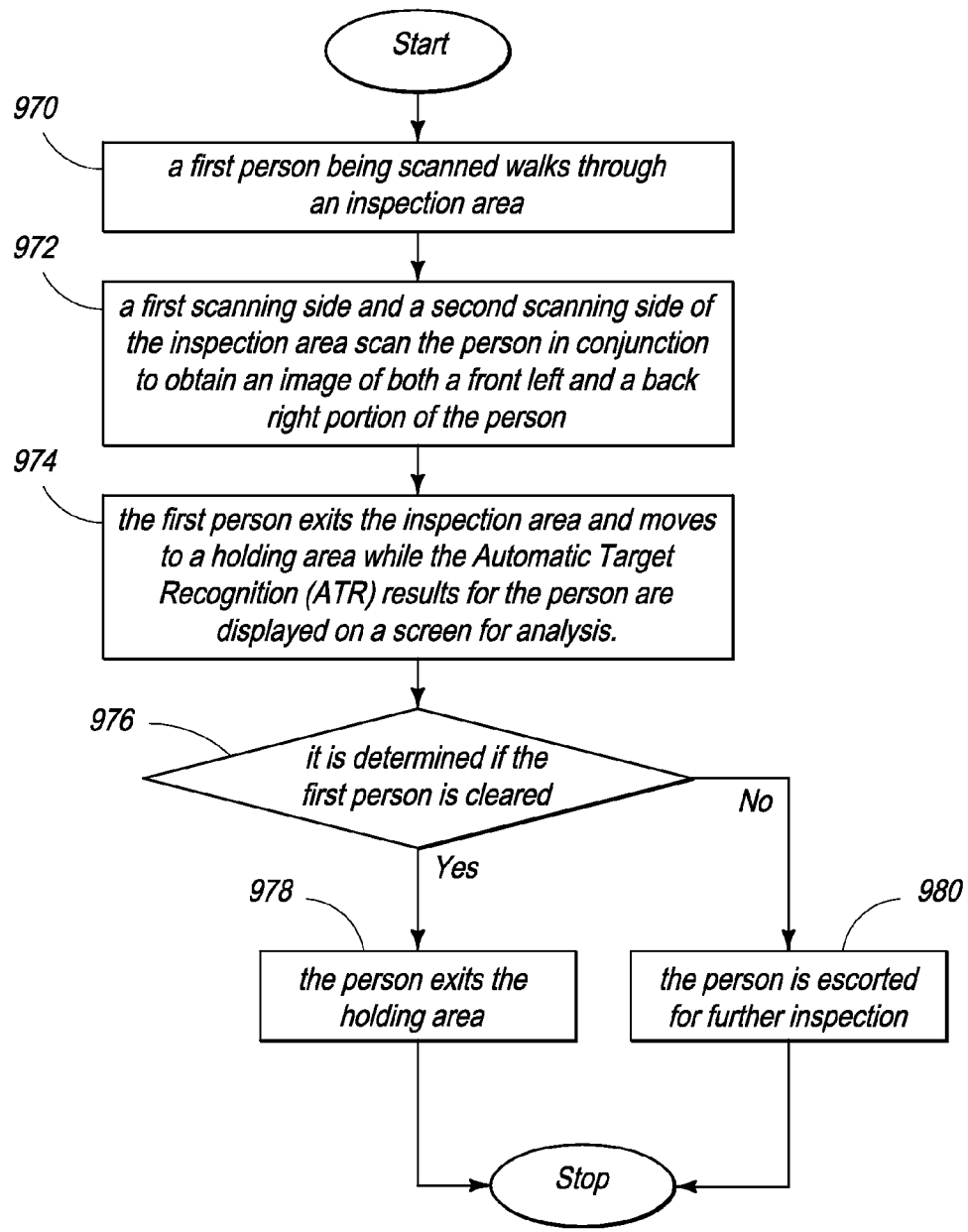
FIG. 9B is a flowchart illustrating the method of using the walk-through implementation of the screening system of the present invention, shown in FIG. 9A.

FIG. 9B is a flowchart illustrating the method of using the walk-through implementation of the screening system of the present invention, shown in FIG. 9A and will be referred to in conjunction with FIG. 9B.

At step 970 a first person being scanned walks through an inspection area defined by the two scanning sides 910 and 920, as illustrated in FIG. 9A. In one embodiment, a person being scanned is conveyed or moved, such as by a moving walkway, through the detection area.

At step 972, as the subject 930 is walking through the system both the first scanning side and second scanning side scan the subject to obtain an image of both a front left and a back right view of the person. In one embodiment, first scanning side 910 and second scanning side 920 scan the subject sequentially, with a minimal time delay between scans. Therefore, subject 930 does not need to turn or stop for scanning; a complete image is produced simply as the person walks through the inspection area 940.

At step 974, the first person exits the screening system 900 and moves to a holding area while the Automatic Target Recognition (ATR) results for the person are displayed on an operator screen for analysis, the resultant generated image can be reviewed at the operator station 950. Since scanning sides comprising a source and detector array are used for imaging, the image produced by each scanning side can also be viewed individually.

Also at step 974, a next person to be scanned walks through the inspection area defined by the two scanning modules.

At step 976 it is determined if the first person is cleared, i.e. if the scanned image of the first person has not revealed a threatening object. If the first person is cleared, he/she exits the holding area at step 978. If the first person is not cleared, he/she is escorted for further inspection at step 980.

The novel design of the walk-through system enables utilization of low-level radiation doses for detection of weapons and dangerous materials, regardless of whether they consist of metal, high-Z or low-Z materials. The radiation dose is in range of less than 20 microrem, preferably less than 10 microrem, more preferably less than 5 microrem and even more preferably less than 1 microrem. This portal configuration can accommodate a high throughput of people as compared to conventional systems because each person being screened simply walks through the portal. Further, the person being screened does not need to stop and turn his or her body as directed by a scanner system operator. In addition, in using such a portal configuration through which the target walks, with its relatively confined area, is easier to combine with other walk-through devices, including metal detectors, drug and explosives sniffers, and video cameras.

It should be appreciated that the inspection system is capable of imaging both metal and non-metal objects (including explosives and non-metal weapons) on a person (including within or under clothing) without the removal of clothing and is capable of processing generated images to only show a body outline and highlight threatening or illegal objects, including both organic and inorganic materials, while hiding private body features, thereby creating a privacy image. The inspection system is configurable such that only the privacy image will be available to the operator. Alternatively, the system may be configurable such that the privacy image is the default image but the raw image, generated prior to processing to only show a body outline and threatening or illegal objects, is still available to the operator.

In various embodiments, the screening system of the present invention provides an improved image resolution, leading to better image interpretation. In an embodiment, an improved image resolution is achieved by decreasing a focal spot generated by one or more X-ray tubes employed in the screening system. A smaller focal spot leads to production of images with a smaller resolution and improved image quality. Also, a smaller resolution in images allows for detection of edges in the image, such as, but not limited to, knife edges. In an embodiment, the one or more X-ray tubes are modified in order to obtain a smaller focal spot. If the power of an X-ray tube is reduced from 140 kV to 70 kV the focal spot size reduces from 1.5 mm×1.5 mm to 0.8 mm×0.8 mm. Since X-ray tubes do not require a power as high as 140 kV for a satisfactory operation of the screening system, reducing the power may lead to achievement of image resolution at least as good as a 20 gauge wire.

Figures 10A, 10B, 10C:
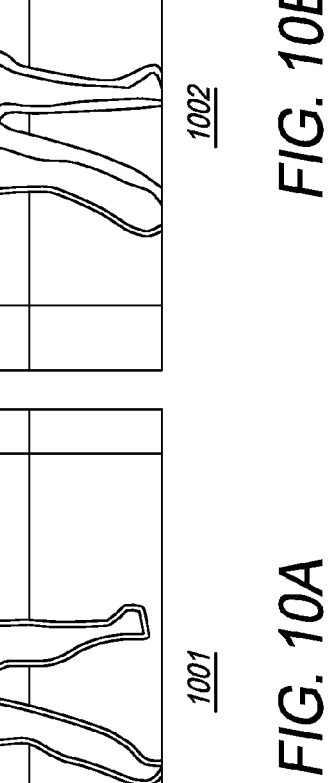
FIG. 10A is an image obtained from using a segmentation algorithm in accordance with one embodiment of the present invention.
FIG. 10B is an image obtained from using a segmentation algorithm in accordance with one embodiment of the present invention.
FIG. 10C is a close view of the segmented object from the image shown in FIG. 10B using a segmentation algorithm in accordance with one embodiment of the present invention.

The image analysis algorithms employed in the present invention also facilitate rapid screening, as it typically takes less than one second to generate an image. Image processing software of the detection system of present invention makes use of appropriate algorithms to reconstruct images such as combining separate front and rear images to create a complete image, as well as for image analysis to determine threats. In one embodiment, a segmentation algorithm is used to distinguish threat objects. An example of use of the segmentation algorithm is illustrated in FIGS. 10A through 10C. Referring to FIG. 10A, image 1001 shows a person free of threats carried on the body (benign subject). In FIG. 10B, image 1002 shows a person carrying a backpack 1003. In order to determine whether the backpack poses a threat, the software uses segmentation algorithm to segment out the backpack 1003 from the image 1002, and generate a separate image 1004 as shown in FIG. 10C. The object size and the pixel intensity of the segmented object are then used to identify threats.

Figure 11B:
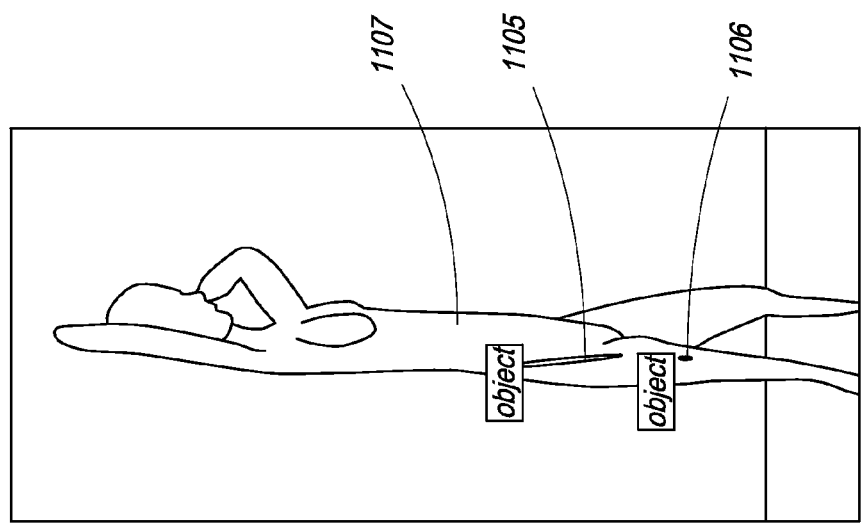
FIG. 11B is an image obtained from using a segmentation algorithm in accordance with one embodiment of the present invention.
Figure 11A:
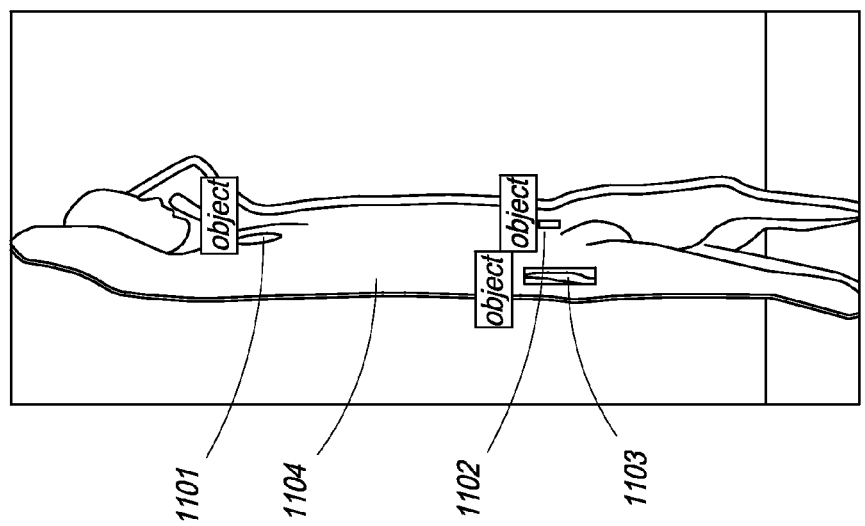
FIG. 11A is an image obtained from using a segmentation algorithm in accordance with one embodiment of the present invention.

The segmentation algorithm is also used to distinguish dark objects on a white background. This feature helps to accurately identify threats comprising absorbing materials, such as metal knives and guns, and ceramic knives. An example of use of this feature of the segmentation algorithm is illustrated in FIGS. 11A and 11B. Referring to FIG. 11A, three potential threat objects 1101, 1102 and 1103 are detected on the individual 1104 being screened. In FIG. 11B, two threat objects 1105, 1106 are detected on the individual 1107 being screened. In both FIGS. 11A and 11B, the same algorithm is used for imaging, with the same parameter settings. From these images, it would be apparent to a person skilled in the art that the image analysis algorithm used by the detection system of the present invention is significantly insensitive to the level of the background. This is because the background is computed from the original image itself, and any potential threats are highlighted. As should be evident to one of ordinary skill in the art, as shown in FIGS. 11A and 11B, the individual's body fills only a partial area of the image. The balance of the image is considered background X-ray scattered signal. Computational methods as simple as averaging or localized smoothing (averaging over localized areas) provide an accurate measure of the background signal level.

Conventionally, for the detection of metallic items concealed on the body of a subject being scanned, an electronic metal detector (EMD) is used in conjunction with X-ray screening systems and data fusion techniques are employed as well. The screening system of the present invention, however, provides a novel technique termed as "Active Background". The Active Background technique takes advantage of the opposing set of detectors in the present screening system that is normally inactive during an X-ray backscatter scan. By using this technique, x-rays that pass by the subject being scanned are captured on the opposing detector and inorganic materials that are off-the-body are identified more easily. The Active Background images are utilized by the same automatic threat detection (ATR) algorithms that process the backscatter images and produce a single integrated decision.

U.S. Pat. Nos. 6,094,472; 6,665,373; and 7,110,493 assigned to the applicant of the present invention are herein incorporated by reference in their entirety.

U.S. patent application Ser. No. 12/887,510, entitled "Security System for Screening People" and U.S. Pat. No. 7,826,589, of the same title, both assigned to the applicant of the present invention, are herein incorporated by reference in their entirety.

U.S. patent application Ser. No. 12/849,987, entitled "Personnel Screening System with Enhanced Privacy" and U.S. Pat. No. 7,796,733, of the same title, both assigned to the applicant of the present invention, are herein incorporated by reference in their entirety.

In addition, U.S. Pat. Nos. 7,418,077 and 7,660,388, entitled "Integrated Carry-On Baggage Cart and Passenger Screening Station" and assigned to the applicant of the present invention are also herein incorporated by reference in their entirety.

In various embodiments, the screening system of the present invention provides a better signal to noise ratio (SNR), due to a plurality of factors. Firstly, the system of the present invention has a wider field of view. A field of view solid angle is measured off a person being inspected. In one embodiment, the amount of the solid angle covered by the detectors is quantified by defining a solid angle relative to a particular place on a person (height off the ground), also the percentage of that solid angle covered by the detectors.

In an embodiment, the operational footprint is reduced to a minimum by reducing the spacing between the two scanning sides of the X-ray screening system of the present invention.

In an embodiment, the dimensions of the screening system of the present invention are 6.5-feet long and 7-feet wide. As is known in the art, angular coverage of an X-ray beam is determined by the angular extent of the X-ray beam as it exits an X-ray source and passes through a collimator. The unique chopper wheel collimator provided by the present invention enables the generated X-ray beam to have a wider field of view. A wide field of view enables at least scanning a person who is six feet and six inches tall from arm to arm, which distance is typically 103 centimeters. In conventional systems, the field of view is typically 54 degrees, which is not wide enough and does not allow for such width of scanning, usually covering 18 centimeters only. Also, in conventional screening systems, for increasing the field of view to allow for wider scanning, the distance between an X-ray source and the object being scanned had to be increased proportionately, thereby increasing the operational footprint of the system.

The screening system of the present invention provides a field of view which is at least 103 centimeters wide, while the person being scanned remains at a distance of only 36 inches from an X-ray source employed in the system. Hence, the screening system of the present invention is slimmer and has a smaller footprint than prior art systems. The area being screened between the two scanning sides can be widely scanned without requiring a large distance between the two scanning sides.

Figure 12:
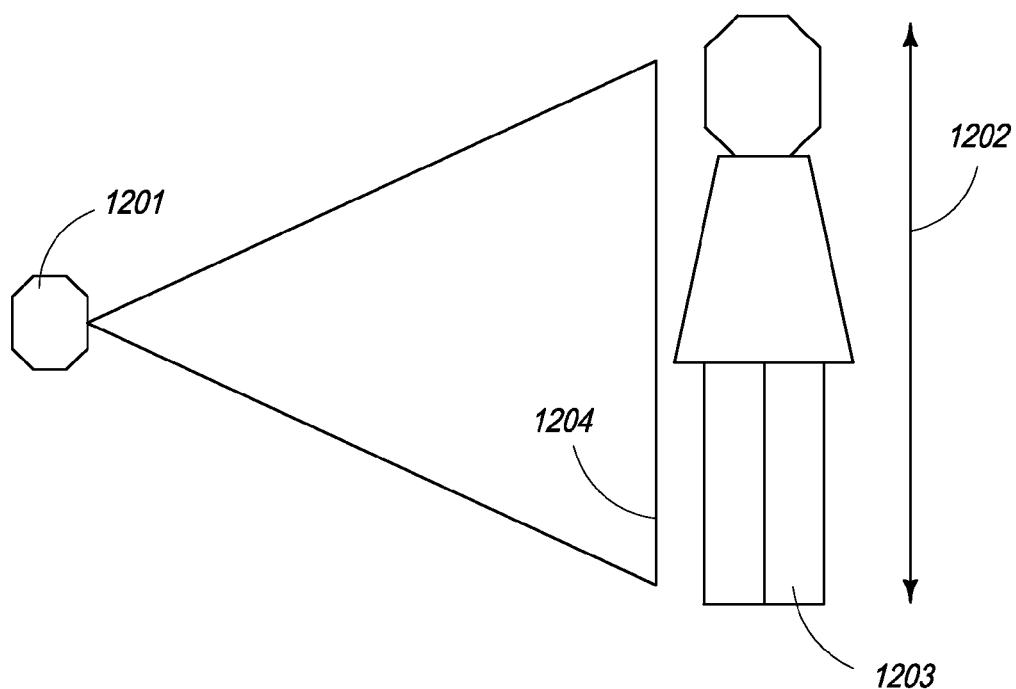
FIG. 12 is a side view diagram illustrating vertical scanning using a single radiation source.

As mentioned earlier, with respect to FIG. 1, the design of the present invention allows for more detector panels to exist in the direct backscatter path, thereby contributing to image quality. The image quality is increased further in another embodiment, by using an approach that increases the area of the detection field and the number of detectors that can be employed. This novel approach is described with reference to FIGS. 12 and 13. FIG. 12 illustrates a side view showing vertical scanning with a single source 1201. In this configuration, the height 1202 of a subject 1203 that can be scanned using the single source 1201 is limited by the view width 1204 or the illumination span of the source.

Figure 13:
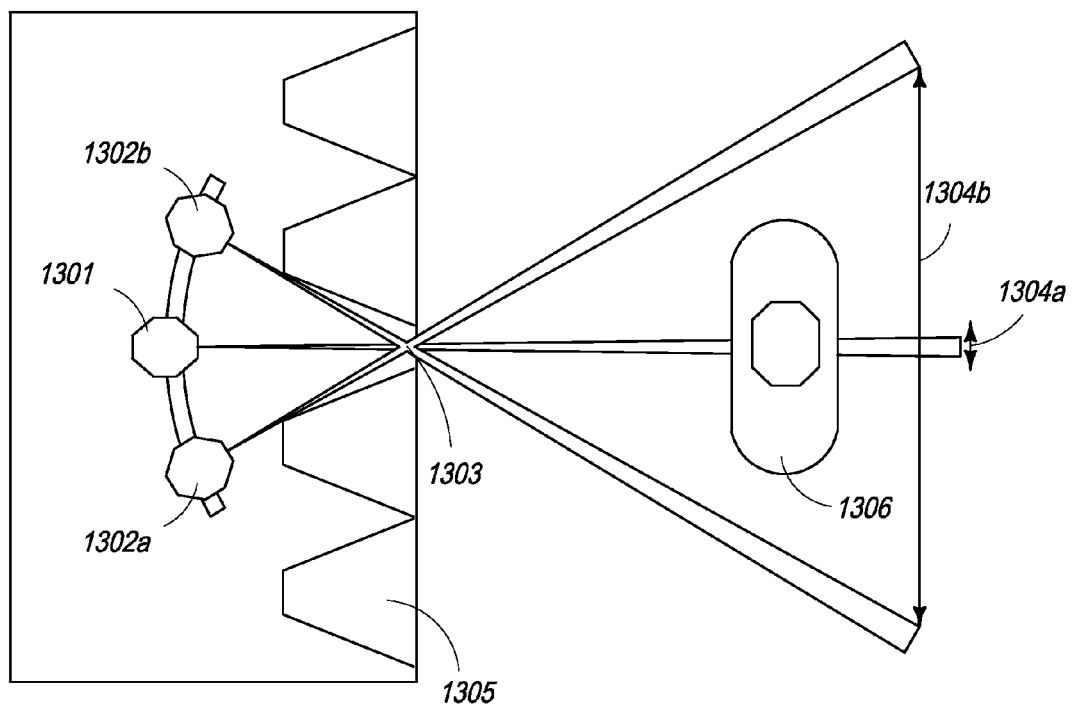
FIG. 13 shows the top view of an exemplary screening arrangement used in the present invention.

To overcome this limitation, the present invention, in one embodiment, employs a novel configuration illustrated in FIG. 13, which shows a top view of an exemplary scanning arrangement. Referring to FIG. 13, the single axis scanning source assembly 1301 is pivoted from point 1302a to 1302b, with a center of rotation 1303 at the front panel of the system. As can be seen from FIG. 13, 1304a is the view width available for the subject 1306, when the source 1301 is fixed, whereas 1304b is the view width available when the source is pivoting. Thus, the view width for a given source expands when it is pivoted. In this case, a larger number of detectors 1305 can be added to the system, thereby providing for an increased detection area. Further, a fixed rectangular opening is provided at the front panel, which also serves as an aperture keeping the focal spot very small in at least one axis. Further, with an optionally pivoting source as shown in FIG. 13, the same system can be employed to perform scans of targets when the person is in motion (and the source is not pivoting) or when the person is stationary (and the source is pivoting). With a stationary target, the image quality is nominally better than when a target is in motion because distortions are caused by differential velocity in the part of the moving subject (e.g., legs and arms). Thus under certain operational situations, the same system could perform a more detailed scan (with the target stationary) if an anomalous object is found on the first scan (when the target is in motion). The choice of system depends upon scanning requirements and is a trade-off between threat detection and high through-put.

Secondly, distribution of electronic components has led to achievement of a better SNR than prior art systems. Conventionally, in screening systems, a video card is placed at a distance from detectors leading to a high SNR ratio as scan images are infected by transmission signals. In various embodiments of the present invention, a plurality of modifications are made to the screening system's circuitry for achieving a better SNR. Firstly, a photomultiplier tube (PMT) card is integrated into a PMT plug. Secondly, analog to digital conversion is performed through a four channel card close to source to reduce transient noise. Thirdly, modified wiring is done specifically to reduced transient noise. Fourthly, a wire mesh is incorporated within composite/carbon fiber walls to create faraday cage for EMI immunity. Fourthly, motion controllers are moved away from other electronics and close to the items they control in order to minimize wiring and electronic interference from the signals within these wires. The above modifications result in much greater contrasted images that appear better than prior art systems.

Thirdly, using a variably increasing X-ray dose in the screening system of the present invention has resulted in an improved SNR over prior art systems. Prior art screening systems were limited to using up to 10 microrem of radiation dose. However, more recent systems are using up to 25 microrem. In various embodiments of the present invention a variable X-ray dose is used, i.e. the X-ray dose (or dwell time) is increased when scanning less sensitive body parts, such as the feet.

In one embodiment of the present invention, a detection signal coming from a PMT is weighted based on which part of the body is being scanned and the relative position of the X-ray source. For example, if the source is pointing toward a particular first region, then signals from the first region are weighted higher than signals outside the first region. Weighting is, therefore, dependent on the instantaneous position of the X-ray source.

Further, as the beam generated by the X-ray source moves faster a scintillator with a faster response is required. A response time of a scintillator is defined as the time to go from one focal spot to next. The screening system of the present invention provides a faster response time than prior art systems, thereby increasing the SNR of the screening system.

Additionally, the system a) comprises an internal safety monitoring circuit to continually monitor safety of system and radiation levels during each scan, b) provides an ionizing radiation dose no greater than 5 micro-rem per scan to any person under inspection, c) scans one side of person in 8 seconds or less, d) shall have a length no greater than 125 cm (length dimension faces person under scan), e) shall have width no greater than 100 cm, f) shall have height no greater than 205 cm, g) shall have an optional wall to aid in privacy of the subject being screened and prevent interference from the background, which will enhance the detection capabilities of the system by making inorganic objects on the side edge of the body more visible in the image and permit full coverage of the body in 2 scans as opposed to 4 scans when the wall is not used, h) shall have an optional communications monitor to facilitate communications between a remote inspector and a local operator and to communicate an image outline of the real body instead of the stick man or a simplified, i.e. "stick man", image with search locations highlighted therein where the image is "calibrated" to adjust for varying body heights of persons relative to the body height of the stick man, i) shall be able to scan a person standing less than two feet, preferably less than one foot, and more preferably no more than 10 inches away, measured from the detector wall to the person's nose, j) shall be capable of communicating to a workstation deployed remote from the scanning system, k) shall be possible to initiate a scan from the remote workstation, l) can be configured to a predefined number of scans per person which shall complete before incrementing to the next person, m) shall permit extra scans to be taken, as an option available to an operator, before incrementing to the next person, n) shall be configurable to force an operator to pass or clear each scan independently, even if multiple scans are required of the same person, o) shall communicate scan results (pass or fail) to a remote operator via visual light indications, which can be remotely viewed by the remote operator, on the local system, i.e. a red light for "fail" and a green light for "pass", p) shall be able to report what operator was logged into the system during which time period and how many persons were scanned by the operator during such period, how many total persons were scanned during each hour of the day, and the number of scans and number of persons scanned in any predefined time period (such as hour, day, or month), q) shall have the option of a training simulator with an image library of at least 100 training images, r) can scan a stationary object having a height of 6 feet 8 inches, or six feet six inches, or less and a width of 45 inches, or 41 inches, or less, and s) can perform scans in 20 seconds, and more preferably 10 seconds, or less. U.S. Pat. No. 7,110,493 is hereby incorporated by reference.

In one embodiment, the system incorporates intelligent auto-detection. In one embodiment, intelligent auto-detection includes passenger or personnel identification in addition to screening. In one embodiment, the identification is via biometric means, such as retinal scans, bioscans, fingerprints and the like. In one embodiment, an ID card is used as verification. In one embodiment, an RFID bracelet is used as identification means. In one embodiment, the identification means is used to store information about the person with which it is associated. Predetermined information may be stored in a computing device that automatically produces information about the person.

In one embodiment, the identification means is used a method for determining the level at which the system operates. For example, if an airline pilot with a pre-determined trust status scans an identification card or identifies himself via biometric means, then he may pass through the scanner at a lower level of radiation, with the knowledge that this person has already been vetted and may not require a full scan. Thus, in one embodiment, the screening system of the present invention can be used at different levels for different people.

U.S. patent application Ser. No. 12/888,412 entitled "Automated Personnel Screening System and Method" and assigned to the applicant of the present invention is herein incorporated by reference in its entirety.

In an embodiment, the layout of the screening system of the present invention provides for "zero clearance", so that the system can be placed directly up against a wall.

Besides being employed for screening of passengers at airports and railway stations, at open and crowded venues such as stadiums and shopping malls, applications of the system of present invention may be extended to inspecting the contents of vehicles and containers at transit points such as ports, border crossings and customs checkpoints etc. In one embodiment, the detection system is implemented as a 'drive-through' system, through which a cargo vehicle to be scanned can be driven, thereby providing a second axis of motion. The detection system of the present invention may also be used for medical purposes.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive.

We claim:
1. A scanning system, comprising:
a first scanning side;
a second scanning side, wherein the first and second scanning sides, in combination, define an inspection area and wherein each of said first scanning side and second scanning side respectively comprises:
a first tower containing a first detection system configured to detect radiation scattered from the person;
a second tower containing a second detection system configured to detect radiation scattered from the person, wherein each of said first tower and second tower, respectively comprises:
a first housing defined by a first side, a second side and a third side that are connected to each other to form a triangular cross-section, wherein the first side has an exterior surface facing the person to receive radiation scattered from the person and an interior surface having a first substrate for receiving and converting said radiation into light, wherein the second side has an interior surface having a second substrate for receiving radiation after it passes through said first side and converting said radiation into light, and wherein the third side is defined by a surface supporting a plurality of photomultiplier tubes and a signal processing board placed proximate said plurality of photomultiplier tubes; and
a third tower containing an X-ray source assembly to generate a pencil beam, wherein the third tower has a front-end strip between an angled left side and an angled right side and wherein the front-end strip has an opening to allow the pencil beam to emanate therefrom for scanning the person, wherein the first tower and the second tower are detachably attached to the third tower so that the attachment abuts the first tower against the angled left side and abuts the second tower against the angled right side of the third tower and wherein said first tower and said second tower are attached on either side of the front-end strip.

2. The scanning system of claim 1, further comprising a second housing proximate said third side of the first housing, wherein said second housing has at least one removable cover to provide access to said signal processing board.

3. The scanning system of claim 1, wherein the scanning system is configured to scan a walking person in a first configuration and scan a stationary person in a second configuration.

4. The scanning system of claim 1, wherein a dose of radiation for scanning is less than 1 microrem.

5. The scanning system of claim 1, wherein the X-ray source assembly comprises an X-ray source, a beam forming apparatus and a motor.

6. The scanning system of claim 3 wherein, in the second configuration, an X-ray source in the X-ray source assembly is pivoted from a first point to a second point with a center of rotation at the front-end strip.

7. The scanning system of claim 1, wherein the signal processing board mounts at least one analog to digital conversion card and a power supply module.

8. The scanning system of claim 1, wherein the first tower, the second tower and the third tower comprise composite/carbon fiber walls that have a wire mesh to create a Faraday cage.

9. The scanning system of claim 1, wherein the first, second and third towers are each physically separate from, and independent of, each other.

10. The scanning system of claim 1, wherein the first, second and third towers are detachable from one another for packaging in a first and a second container for transportation.

11. The scanning system of claim 3, wherein, when in the first configuration, the system is configured to scan a side of the person in 8 seconds or less.

12. The scanning system of claim 1, wherein the system has a length no greater than 125 cm, a height no greater than 205 cm and a width no greater than 100 cm.

13. The scanning system of claim 3, wherein, in a second configuration, the system is configured to perform a scan of the person at a distance no more than 10 inches away from either the first or the second scanning side, and wherein said distance is measured from the person's nose to the exterior surface of the first side of the first or second towers of either the first or the second scanning side.

14. The scanning system of claim 3, wherein, in the second configuration, the system is configured to perform a scan of the person and wherein the person has a height up to 6 feet 8 inches and a width up to 45 inches.

15. The scanning system of claim 3, wherein, in the second configuration, the system is configured to perform a complete scan of the person while the person faces one of either the first or the second scanning side and holds a pose for approximately 6 seconds for scanning.

16. The scanning system of claim 15, wherein the pose comprises the person placing his or her hands forward with fingertips touching his or her head.

17. A method of assembling a scanning system at an inspection site, the method comprising:
    transporting at least one container to the inspection site, wherein said at least one container comprises:
        a first tower containing a first detection system configured to detect radiation scattered from a person;
        a second tower containing a second detection system configured to detect radiation scattered from the person, wherein each of said first and second towers comprise a first housing defined by a first side, a second side and a third side that are connected to each other in a polygonal cross-section, wherein the third side is defined by a surface supporting a plurality of photomultiplier tubes and a signal processing board placed proximate said plurality of photomultiplier tubes;
        a third tower containing an X-ray source assembly to generate a pencil beam, wherein the third tower has a front-end surface between an angled left side and an angled right side and wherein the front-end surface has an opening to allow the pencil beam to emanate therefrom for scanning the person; and
        a base;
    attaching said first tower, second tower, and third tower to the base; and
    attaching the first tower and the second tower to the third tower so that the first tower abuts the angled left side and the second tower abuts the angled right side of the third tower, wherein said first tower and said second tower are attached on either side of the front-end surface.

18. The method of claim 17, wherein the X-ray source assembly comprises an X-ray source, a beam forming apparatus and a motor.

19. The method of claim 18, wherein the X-ray source is pivoted from a first point to a second point with a center of rotation at the front-end surface.

20. The method of claim 18, wherein the beam forming apparatus comprises a spin-roll chopper.

21. The method of claim 20, wherein the spin-roll chopper comprises a hollow cylinder having at least two helical slits and wherein a width of the helical slits varies along a length of hollow cylinder.

22. The method of claim 21, wherein the width of the helical slits increases from portions away from the X-ray source to portions closer to the X-ray source.

23. The method of claim 21, wherein the helical slits provide scan angles ranging from 60 degrees to 90 degrees by varying at least one of the following:
    a distance of the spin-roll chopper from the X-ray source and the person;
    a height of the hollow cylinder; or
    a diameter of the hollow cylinder.

* * * * *